US008598223B2

(12) United States Patent
Takeuchi et al.

(10) Patent No.: US 8,598,223 B2
(45) Date of Patent: Dec. 3, 2013

(54) CRYSTALLINE FORMS OF 4, 4'-[4-FLUORO-7-({4-[4-(3-FLUORO-2-METHYLPHENYL) BUTOXY] PHENYL} ETHYNYL)-2-METHYL-1H-INDOLE-1,3-DIYL] DIBUTANOIC ACID, 4,4'-[2-METHYL-7-({4-[4-(PENTAFLUORO-PHENYL) BUTOXY] PHENYL} ETHYNYL)-1H-INDOLE-1, 3-DIYL] DIBUTANOIC ACID, AND 4,4'-[4-FLUORO-2-METHYL-7-({4-[4-(2, 3, 4, 6-TETRAFLUOROPHENYL) BUTOXY] PHENYL} ETHYNYL)-1H-INDOLE-1, 3-DIYL] DIBUTANOIC ACID

(75) Inventors: Jun Takeuchi, Osaka (JP); Satoshi Itadani, Osaka (JP); Junya Ueda, Osaka (JP); Shizuka Ono, Osaka (JP); Takahiro Nekado, Osaka (JP); Manabu Fujita, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/805,689

(22) PCT Filed: Jun. 20, 2011

(86) PCT No.: PCT/JP2011/064088
§ 371 (c)(1),
(2), (4) Date: Dec. 20, 2012

(87) PCT Pub. No.: WO2011/162222
PCT Pub. Date: Dec. 29, 2011

(65) Prior Publication Data
US 2013/0090482 A1    Apr. 11, 2013

(30) Foreign Application Priority Data
Jun. 21, 2010 (JP) ................. 2010-140344

(51) Int. Cl.
*A61K 31/405* (2006.01)
*A61K 31/40* (2006.01)
*C07D 209/04* (2006.01)

(52) U.S. Cl.
USPC ............... 514/415; 514/419; 548/491

(58) Field of Classification Search
USPC ................. 548/491; 514/415, 419
See application file for complete search history.

(56) References Cited

U.S. PATENT DOCUMENTS

| 5,137,910 | A  | 8/1992  | Gray et al.      |
| 5,229,413 | A  | 7/1993  | Gray et al.      |
| 5,530,019 | A  | 6/1996  | Okada et al.     |
| 5,965,745 | A  | 10/1999 | Brown et al.     |
| 6,057,317 | A  | 5/2000  | Guillaumet et al.|
| 6,833,387 | B1 | 12/2004 | Faull et al.     |
| 7,728,023 | B2 | 6/2010  | Takeuchi et al.  |
| 7,763,610 | B2 | 7/2010  | Takeuchi et al.  |
| 8,115,014 | B2 | 2/2012  | Ohmoto et al.    |
| 2006/0194797 | A1 | 8/2006 | Takeuchi et al. |
| 2008/0188532 | A1 | 8/2008 | Takeuchi et al. |
| 2010/0160647 | A1 | 6/2010 | Ohmoto et al.   |
| 2010/0234368 | A1 | 9/2010 | Takeuchi et al. |

FOREIGN PATENT DOCUMENTS

| AU | 04 268865       | 3/2005  |
| EP | 0 405 116       | 1/1991  |
| EP | 1 661 892       | 5/2006  |
| EP | 1 852 420       | 11/2007 |
| JP | 11-92476        | 8/1989  |
| JP | 03 047123       | 2/1991  |
| JP | 07 507574       | 8/1995  |
| JP | 10 512291       | 11/1998 |
| JP | 02/536362       | 10/2002 |
| JP | 2010-168359     | 8/2010  |
| JP | 2010-168359 A   | 8/2010  |
| JP | 11-136551       | 7/2011  |
| WO | WO-02/00646     | 1/2002  |
| WO | WO-03/074051    | 9/2003  |
| WO | WO-03/082271    | 10/2003 |
| WO | WO 03/091215 A1 | 11/2003 |
| WO | WO 2004/007451 A1 | 1/2004 |
| WO | WO-2004/099192  | 11/2004 |
| WO | WO-2005/021518  | 3/2005  |
| WO | WO 2005/021518 A1 | 3/2005 |
| WO | WO-2006/090817  | 8/2006  |
| WO | WO 2006/090817 A1 | 8/2006 |

OTHER PUBLICATIONS

Julia, M. et al., "No. 386.—Recherches en serie indolique. VII.—Sur la Cyclisation des alpha-arylaminocetones," Bulletin de la Societe Chimique de France, 1962, pp. 2263-2267.
Lenzi et al., "A series of alpha-arylamino ketones was cyclized by simple heating to the corresponding indoles," STN Tokyo, 1963; English Translation of Julia, M. et al., "No. 386.—Recherches en serie indolique. VII.—Sur la Cyclisation des alpha-arylaminocetones," Bulletin de la Societe Chimique de France, 1962, pp. 2263-2267.
Daines, Robert A. et al., "First X-ray Cocrystal Structure of a Bacterial FabH Condensing Enzyme and a small Molecule Inhibitor Achieved Using Rational Design and Homology Modeling," J. Med. Chem., 2003, vol. 46, pp. 5-8.
Rajur, Sharanabasava B. et al., "Synthesis of 1,2,3,4-tetrahydropyrazino-[1,2-a] indoles and ethyl 1-(2-amino-ethyl) indole-2-carboxylates," Indian Journal of Chemistry, Dec. 1989, vol. 28B, pp. 1065-1068.
Basanagoudar, L. D. et al., "Synthesis of 10-phenyl-1,2,3,4-tetrahydropyrazino[1,2-a]indoles and ethyl 1-(2-aminoethyl)-3-phenylindole-2-carboxylates," Indian Journal of Chemistry, Nov. 1991, vol. 30B, pp. 1014-1017.

(Continued)

*Primary Examiner* — Shawquia Young
(74) *Attorney, Agent, or Firm* — Millen, White, Zelano & Branigan, P.C.

(57) ABSTRACT

The present invention provides type C crystal of compound I, type B crystal of compound II, or type C crystal of compound III set forth in this specification.

15 Claims, 8 Drawing Sheets

(56) References Cited

OTHER PUBLICATIONS

Salituro, Francesco G. et al., "3-(2-Carboxyindol-3-yl) propionic Acid-Based Antagonist of the N-Methyl-D-aspartic Acid Receptor Associated Glycine Binding Site," J. Med. Chem., 1992, vol. 35, pp. 1791-1799.
Di Fabio, R. et al., "Substituted Indole-2-carboxylates as in Vivo Potent Antagonists Acting as the Strychnin-Insensitive Glycine Binding Site," J. Med. Chem., 1997, vol. 40, pp. 841-850.
Heinrich, T et al., "A New Synthesis of indole 5-carboxylic acids and 6-hydroxy-indole-5-carboxylic acids in the preparation of an o-hydroxylated metabolite of vilazodonem," Bioorganic & Medicinal Chemistry Letters, 2004, vol. 14, pp. 2681-2684.
Stella, Valentino J., "Prodrugs as therapeutics," Expert Opin. Ther. Patents, 2004, vol. 14, No. 3, pp. 277-280.
Wolff, Manfred E., "vol. 1: Principles and Practice," Burger's Medicinal Chemistry and Drug Discovery: Fifth Edition, Mar. 16, 1995.
Ettmayer, Peter et al., "Lessons Learned from Marketed and Investigational Prodrugs," Journal of Medicinal Chemistry, May 6, 2004, vol. 47, No. 10.
Vippagunta, Sudha R. et al., "Crystalline solids," Advanced Drug Delivery Reviews, 2001, vol. 48, pp. 3-26.
Morissette, Sherry L. et al., "High-throughput crystallization: polymorphs, salts, co-crystals and solvates of pharmaceutical solids," Advanced Drug Delivery Reviews, 2004, vol. 56, pp. 275-300.
Testa, Bernard, "Prodrug research: futile or fertile?" Biochemical Pharmacology 68 (2004) 2097-2106.
Touzeau, F. et al., "Synthesis and Biological Evaluation of New 2-(4,5-Dihydro-1H-imidazol-2-yl)-3,4-dihydro-2H-1,4-benzoxazine Derivatives," J. Med. Chem., 2003, vol. 46, pp. 1962-1979.
Mayer, Stanislas et al., "Regioselective formylation of ethyl 3,4-dihydro-2H-1,4-Benzoxazine-2-Carboxylate or 2-acetate derivatives," Heterocycles, 2001, vol. 55, No. 10.
West, A. R., "Solid State Chemistry and its applications," Mar. 3, 1988, Wiley, New York.
Office Action for U.S. Appl. No. 11/885,018, dated Feb. 3, 2009.
Office Action for Related U.S. Appl. No. 10/569,482 dated Feb. 11, 2009.
Office Action for Related U.S. Appl. No. 10/569,482 dated Oct. 13, 2009.
Office Action for Related U.S. Appl. No. 12/644,378, dated Nov. 12, 2010.
Office Action for related Australian Patent Application No. 2006216170, dated Jan. 5, 2011.
Office Action for Australian Patent Application No. 2004268865, dated Nov. 12, 2009.
Office Action for related Canadian Patent Application No. 2537355, dated Mar. 28, 2011.
Office Action for Chinese Patent Application No. 200910260865, dated Sep. 7, 2011.
English Translation of Office Action for Chinese Patent Application No. 200910260865.0, dated Sep. 7, 2011.
First Office Action for Chinese Patent Application No. 200680005791.0, dated Sep. 18, 2009.
First Office Action for Chinese Patent Application No. 200480025056.7, dated Feb. 22, 2008.
Second Office Action for Chinese Patent Application No. 200480025056.7, dated Jan. 22, 2010.
English Translation of Decision on Rejection for Chinese Patent Application No. 200680005791.0, dated Oct. 12, 2010.
Office Action for European Patent Application No. 04772519.7-2117, dated Jan. 2, 2010.
Second Office Action for European Patent Application No. 04772519.7-2117, dated Aug. 9, 2010.
Third Office Action for related European Patent Application No. 04772519.7, dated Mar. 23, 2011.
European Search Report for European Application No. 09180244, dated Apr. 26, 2010.
Office Action for Indian Patent Application No. 756/KOLNP/2006, dated Oct. 2, 2009.
Office Action for Israeli Patent Application No. 173898, dated Feb. 3, 2010.
English Translation of Office Action for the Israeli Patent Application No. 173898, dated Feb. 3, 2010.
Office Action for the Israeli Patent Application No. 185199, dated May 26, 2010.
English Translation of Office Action for Israeli Patent Application No. 185199, dated May 26, 2010.
Office Action for Japanese Patent Application No. 2005 513507, dated Jun. 22, 2010.
Office Action for Japanese Patent Application No. 2009-289494, dated Nov. 29, 2011.
English Translation of Office Action for Japanese Patent Application No. 2009-289494, dated Nov. 29, 2011.
Office Action for Related Japanese Patent Application No. 2011-136551, dated Dec. 20, 2012.
English Abstract of JP 2011-136551, Publication Date: Jul. 14, 2011.
English Translation of Patent Application No. 2011-136551, Publication Date: Jul. 14, 2011.
English Abstract of JP-2011-092476, Kawasaki Steel Corp., "Manufacture of Welded Steel Pipe," Publication Date: Aug. 2, 1989.
English Abstract of JP 2010-168359, Publication Date: Aug. 5, 2010.
English Abstract of JP-2002-536362, Publication Date: Oct. 29, 2009, Data supplied from the espacenet database-Worldwide on Jul. 20, 2010.
Office Action for New Zealand Patent Application No. 545666, dated Dec. 5, 2008.
Office Action for New Zealand Patent Application No. 560513, Jul. 9, 2009.
Office Action for Russian Patent Application No. 2006110513/04, dated Jul. 5, 2008.
Office Action for Russian Patent Application No. 2007135347/04, Feb. 3, 2010.
Second Office Action for Russian Patent Application No. 2007135347/04, dated May 12, 2010.
English Translation of Second Office Action for Russian Patent Application No. 2007135347/04 dated May 12, 2010.
Written Opinion of the International Searching Authority for PCT/JP2011/064088, dated Aug. 2, 2011.
International Search Report of PCT/JP2011/064088 (Jul. 15, 2011).
Abstract of JP 2010-168359 A (Aug. 5, 2010).

CRYSTALLINE FORMS OF 4, 4'-[4-FLUORO-7-({4-[4-(3-FLUORO-2-METHYLPHENYL) BUTOXY] PHENYL} ETHYNYL)-2-METHYL-1H-INDOLE-1,3-DIYL] DIBUTANOIC ACID, 4,4'-[2-METHYL-7-({4-[4-(PENTAFLUOROPHENYL) BUTOXY] PHENYL} ETHYNYL)-1H-INDOLE-1, 3-DIYL] DIBUTANOIC ACID, AND 4,4'-[4-FLUORO-2-METHYL-7-({4-[4-(2, 3, 4, 6-TETRAFLUOROPHENYL) BUTOXY] PHENYL} ETHYNYL)-1H-INDOLE-1, 3-DIYL] DIBUTANOIC ACID

TECHNICAL FIELD

The present invention relates to new crystalline forms of 4,4'-[4-fluoro-7-({4-[4-(3-fluoro-2-methylphenyl)butoxy]phenyl}ethynyl)-2-methyl-1H-indole-1,3-diyl]dibutanoic acid (hereinafter sometimes abbreviated to compound I), 4,4'-[2-methyl-7-({4-[4-(pentafluorophenyl)butoxy]phenyl}ethynyl)-1H-indole-1,3-diyl]dibutanoic acid (hereinafter sometimes abbreviated to compound II), and 4,4'-[4-fluoro-2-methyl-7-({4-[4-(2,3,4,6-tetrafluorophenyl)butoxy]phenyl}ethynyl)-1H-indole-1,3-diyl]dibutanoic acid (hereinafter sometimes abbreviated to compound III).

BACKGROUND ART

Bronchial asthma is a pathological condition where the airway is constricted by airway contraction or inflammation, which causes paroxysmal coughing, stridor, and dyspnea. Therapeutic agents for bronchial asthma include inhaled steroids, which have potent anti-inflammatory effects, β stimulants or theophyllines which are bronchodilating agents, and agents which inhibit the activity of chemical mediators, etc.

Histamines, leukotrienes, prostaglandins, and the like are known as chemical mediators which are released from mast cells or inflammatory cells involved in bronchial asthma. Among leukotrienes (LTs), cysteinyl leukotrienes (hereinafter, referred to as "cysLTs") represented by $LTC_4$, $LTD_4$ and $LTE_4$ have an approximately 1,000-fold stronger airway contractile effect as compared to histamine. Moreover, cysLTs promote induction of airway inflammation, typically by inflammatory cell infiltration, increased airway hypersensitivity and mucus secretion in the airway, by which they are deeply involved in the underlying pathological condition of bronchial asthma.

CysLTs are physiologically active substances in vivo which are 5-lipoxygenase metabolites of arachidonic acid. There are at least two different types of receptors for cysLTs, wherein $cysLT_1$ receptor and $cysLT_2$ receptor have been cloned to date (Nature, 399, 789-793, 1999, J. Biol., Chem., 275, 30531-30536, 2000). $CysLT_1$ receptor is expressed primarily in airway smooth muscle, and deeply relates to the onset of bronchial asthma (Am. J. Respir. Crit. CareMed., 163, 226-233, 2001). Meanwhile, it has been reported that $cysLT_2$ receptor adopts $LTC_4$, $LTD_4$, and $LTE_4$ as a ligand, similar to the $cysLT_1$ receptor, and is expressed in bronchial smooth muscle (J. Biol. Chem., 275, 30531-30536, 2000, Am. J. Respir. Crit. CareMed., 164, 2098-2101, 2001).

Pranlukast hydrate, Montelukast sodium and Zafirlukast are currently commercially available leukotriene receptor antagonists, and they are used as an oral drug for treating bronchial asthma and/or an oral drug for treating allergic rhinitis.

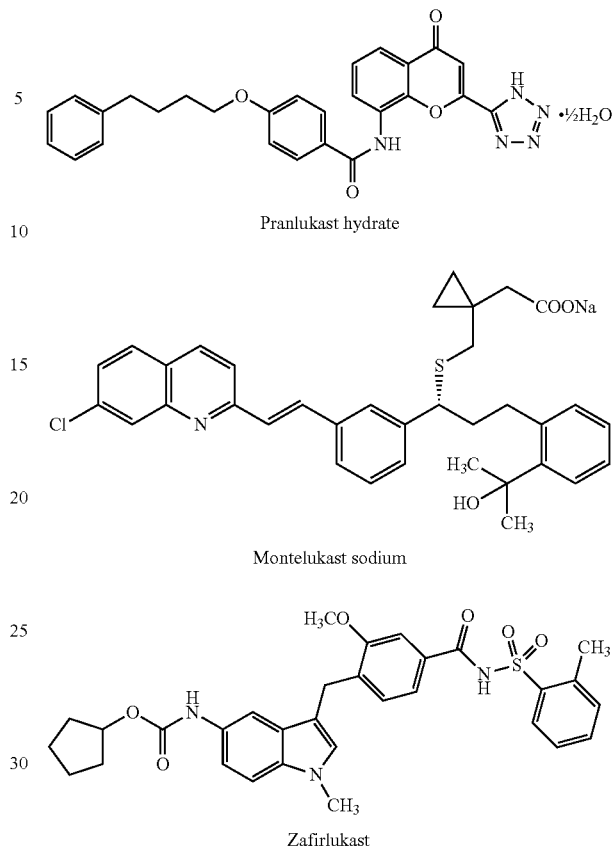

Pranlukast hydrate

Montelukast sodium

Zafirlukast

However, it is known that these leukotriene receptor antagonists are more effective for mild or moderate bronchial asthma than for severe ones. It is also known that there exist some non-responders whom the pharmaceutical agent does not have sufficient effects in mild or moderate bronchial asthma. Accordingly, there has been a demand for agents having a higher therapeutic activity than the existing agents.

One of the means for accomplishing the object is to enhance a leukotriene receptor antagonistic activity of the agents. The currently commercially available three compounds are all $cysLT_1$ antagonists. As approaches to potentiate the receptor antagonistic activity, a method of further enhancing a $cysLT_1$ antagonistic activity and a method of constructing a combination of $cysLT_1$ antagonistic activity and $cysLT_2$ antagonistic activity are devised.

Meanwhile, antiasthmatic drugs are required to be medicated on a regular basis and therefore oral preparations are preferred which are convenient for taking medicine. Among oral preparations, drugs with less dosing frequencies are preferred for convenience of medication. Namely, an oral anti-asthma drug is preferred having a long-term activity. With regard to development of oral preparations, it is very important to improve the duration of drug efficacy.

However, particularly in oral preparations, a compound that is of interest per se may be labile; may exhibit poor delivery to the target organ; may exhibit early metabolism and excretion even though an antagonistic activity of the compound is potent. For these reasons, it is not easy to obtain a compound having long-lasting potent effects.

Patent Document 1 describes that a compound represented by the general formula (A):

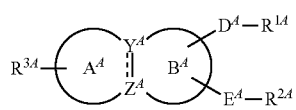

wherein $R^{1A}$ and $R^{2A}$ each independently represent an acidic group which may be protected, $D^A$ and $E^A$ each independently represent a bond or a spacer which has a main chain having 1 to 8 atoms, $R^{3A}$ represents a substituent, ring $A^A$ represents a cyclic group which may further have substituent(s), ring $B^A$ represents a cyclic group which may further have substituent(s), $Y^A$ and $Z^A$ each independently represent a carbon atom or a nitrogen atom,

..........

represents a single bond or a double bond, wherein when $Y^A$ and/or $Z^A$ represents a nitrogen atom, the bond represents a single bond, has cysLT$_2$ receptor antagonistic effects. However, there is no disclosure or suggestion of which ring specifically contributes to the duration of drug efficacy, even though a variety of ring-fused compounds are disclosed therein.

Patent Document 2 describes that a compound shown by the general formula (B)

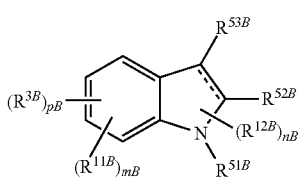

wherein $R^{11B}$ and $R^{12B}$ each independently represent a substituent, two groups selected from $R^{51B}$, $R^{52B}$ and $R^{53B}$ each independently represent a group having an acidic group which may be protected, the other one of $R^{51B}$, $R^{52B}$ and $R^{53B}$ represents a hydrogen atom or a substituent, $R^{3B}$ represents

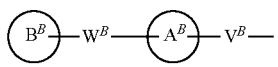

wherein $V^B$ and $W^B$ each independently represent a bond or a spacer which has a main chain having 1 to 8 atoms, ring $A^B$ and ring $B^B$ each independently represent a cyclic group which may have substituent(s) or the like, mB represents 0 or an integer of 1 to 4, nB represents 0 or an integer of 1 to 2, pB represents 0 or 1,

..........

represents a single bond or a double bond, provided that a sum of mB and pB is an integer less than or equal to 4 (explanation of the groups excerpted a necessary part), has potent leukotrien receptor antagonistic effects, in combination with an excellent oral activity. However, even though various kinds of substituents are described in the afore-referenced Patent Document, there is no disclosure or suggestion of effects that may be obtained based on the kind of substituents and/or substitution positions. Particularly, Patent Document 2 is completely silent on a scheme to improve the duration of drug efficacy with retaining a potent oral activity. Furthermore, in Patent Document 2, the exemplified compound wherein $V^B$ represents a triple bond is only 4-(1-(carboxymethyl)-7-{[2-hydroxy-4-(4-phenoxybutoxy)phenyl]ethynyl}-1H-indol-3-yl)butanoic acid described in Example 101.

Furthermore, in Japanese Unexamined Published Patent Application No. 2010-168359 (hereinafter, sometimes abbreviated to Patent Document 3), compound I, compound II, and compound III are described in Example 14(2), 9, and 14(3), respectively.

PRIOR ART DOCUMENTS

Patent Documents

[Patent Document 1] International Publication number WO 2005/021518
[Patent Document 2] International Publication number WO 2006/090817
[Patent Document 3] Japanese Unexamined Published Patent Application No. 2010-168359

SUMMARY OF THE INVENTION

Problems to be Resolved by the Invention

There is a demand of a cysLT$_1$/cysLT$_2$ receptor antagonist having potent oral activity and long-lasting effects.

Furthermore, it is known that crystalline compounds may have some crystalline polymorphs. Compounds having some crystalline polymorphs have a different solubility, solubility rate, or stabilities to heat, light, or moisture, depending on their crystalline forms. Therefore, with regard to development of pharmaceuticals, it is very important to select the crystalline form of the bulk drug suitable for its indications and dosage form.

Recently, there is an example that in certain lot of a commercially available product, a new crystalline polymorph was identified, the production was therefore discontinued. Therefore, there was a need that the most stable crystal which is very unlikely to transform to another crystalline polymorph was developed and supplied stably from the initial stage of development.

Disclosure of the Invention

The inventors researched crystalline polymorphs of compound I, compound II, or compound III earnestly in view of these problems.

For example, with respect to compound I, various conditions for crystallization were tested by changing a combination of solvents, temperature or the like. The inventors found that the majority of the resulting crystals was type A crystal as described in Patent Document 3, while a new type B crystal was identified, and compound I had a crystalline polymorph. As a result of further investigation, a new type C crystal was found from differential scanning calorimetry (DSC) of type B crystal.

The inventors evaluated the crystalline polymorph of compound I with a variety of tests, and found that type C crystal had improved thermodynamically stability, photostability, and humidity stability, and defined type C crystal as the most stable crystal of compound I. However, frequency of obtaining compound I as type C crystal was really low, i.e. 0.8% (7/917) to get containing type C crystal, and 0.3% (3/917) to get pure type C crystal among the whole crystalline polymorph screening conditions, and type C crystal was obtained by limited condition only. Furthermore, the condition was not satisfactory for providing large amounts of the compound as a medicine stably.

Therefore, the inventors further investigated in order to solve these problems, and found the limited condition to get type C crystal which is the most stable crystal of compound I, in which they succeeded to obtain large amounts of type C crystal stably in high purity.

In addition, in compound II and compound III, the inventors succeeded to obtain large amounts of new stable crystals stably in high purity.

Therefore, the inventors found that newly found type C crystal of compound I, type B crystal of compound II, or type C crystal of compound III (hereinafter, these crystalline forms are sometimes abbreviated to the crystalline form of the present invention) had improved photostability and humidity stability, and were thermodynamically stable, and therefore the compounds can be stably supplied for technical application. Furthermore, the inventors succeeded to obtain large amounts of the crystalline form of the present invention stably in high purity.

Furthermore, the inventors found that the crystalline form of the present invention antagonized a $cysLT_1$/$cysLT_2$ receptor potently, and the compound had potent oral activity and long-lasting effects. The present invention have been achieved by the finding that the crystalline form of the present invention is useful as a therapeutic drug for respiratory diseases.

Therefore, the present invention relates to:

(1) A crystal of 4,4'-[4-fluoro-7-({4-[4-(3-fluoro-2-methylphenyl)butoxy]phenyl}ethynyl)-2-methyl-1H-indole-1,3-diyl]dibutanoic acid having at least peaks of about 7.29, 10.24, 12.15, 17.95, and 18.44 at 2θ degree in powdered X-ray diffraction spectrum, (2) The crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to above item (1), having peaks of about 6.41, 7.29, 9.22, 10.03, 10.24, 12.15, 12.59, 13.36, 13.88, 14.15, 14.44, 16.60, 17.33, 17.95, 18.44, 18.86, 19.27, 20.23, 21.10, 21.85, 22.26, 23.11, 23.63, and 24.38 at 2θ degree in powdered X-ray diffraction spectrum, (3) The crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to above item (2), characterized by the chart of powdered X-ray diffraction spectrum shown in FIG. 3, (4) A crystal of 4,4'-[4-fluoro-7-({4-[4-(3-fluoro-2-methylphenyl)butoxy]phenyl}ethynyl)-2-methyl-1H-indole-1,3-diyl]dibutanoic acid having an endothermic peak of about 157° C. in differential scanning calorimetry, (5) The crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to above item (4), characterized by the chart of differential scanning calorimetry shown in FIG. 4, (6) The crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to above item (1), having an endothermic peak of about 157° C. in differential scanning calorimetry, (7) A crystal of 4,4'-[2-methyl-7-({4-[4-(pentafluorophenyl)butoxy]phenyl}ethynyl)-1H-indole-1,3-diyl]dibutanoic acid having at least peaks of about 5.12, 10.16, 10.51, 14.90, and 20.42 at 2θ degree in powdered X-ray diffraction spectrum, (8) The crystal of 4,4'-[2-methyl-7-({4-[4-(pentafluorophenyl)butoxy]phenyl}ethynyl)-1H-indole-1,3-diyl]dibutanoic acid according to above item (7), having peaks of about 5.12, 8.94, 9.22, 10.16, 10.51, 12.07, 13.07, 13.62, 14.37, 14.90, 15.35, 16.05, 16.92, 17.52, 17.86, 18.61, 19.58, 19.92, 20.42, 21.19, 21.71, 22.03, 22.39, 23.74, and 24.24 at 2θ degree in powdered X-ray diffraction spectrum, (9) The crystal of 4,4'-[2-methyl-7-({4-[4-(pentafluorophenyl)butoxy]phenyl}ethynyl)-1H-indole-1,3-diyl]dibutanoic acid according to above item (8), characterized by the chart of powdered X-ray diffraction spectrum shown in FIG. 5,

(10) A crystal of 4,4'-[2-methyl-7-({4-[4-(pentafluorophenyl)butoxy]phenyl}ethynyl)-1H-indole-1,3-diyl]dibutanoic acid having an endothermic peak of about 146° C. in differential scanning calorimetry,

(11) The crystal of 4,4'-[2-methyl-7-({4-[4-(pentafluorophenyl)butoxy]phenyl}ethynyl)-1H-indole-1,3-diyl]dibutanoic acid according to above item (10), characterized by the chart of differential scanning calorimetry shown in FIG. 6,

(12) The crystal of 4,4'-[2-methyl-7-({4-[4-(pentafluorophenyl)butoxy]phenyl}ethynyl)-1H-indole-1,3-diyl]dibutanoic acid according to above item (7), having an endothermic peak of about 146° C. in differential scanning calorimetry,

(13) A crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid having at least peaks of about 5.25, 12.16, 15.08, 17.07, and 21.44 at 2θ degree in powdered X-ray diffraction spectrum,

(14) The crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to above item (13), having peaks of about 5.25, 8.12, 8.92, 10.45, 11.19, 12.16, 13.12, 13.51, 14.54, 15.08, 15.65, 16.25, 17.07, 17.80, 18.61, 19.59, 20.21, 20.75, 21.44, 22.23, 22.53, 23.29, and 24.41 at 2θ degree in powdered X-ray diffraction spectrum,

(15) The crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to above item (14), characterized by the chart of powdered X-ray diffraction spectrum shown in FIG. 9,

(16) A crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid having an endothermic peak of about 152° C. in differential scanning calorimetry,

(17) The crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to above item (16), characterized by the chart of differential scanning calorimetry shown in FIG. 10,

(18) The crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to above item (13), having an endothermic peak of about 152° C. in differential scanning calorimetry,

(19) A pharmaceutical composition containing the crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to any one of above items (1) to (6) as an active ingredient,

(20) A pharmaceutical composition containing the crystal of 4,4'-[2-methyl-7-({4-[4-(pentafluorophenyl)butoxy]phenyl}ethynyl)-1H-indole-1,3-diyl]dibutanoic acid according to any one of above items (7) to (12) as an active ingredient,

(21) A pharmaceutical composition containing the crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to any one of above items (13) to (18) as an active ingredient,

(22) The composition according to above items (19) to (21), which is a cysLT$_1$/cysLT$_2$ receptor antagonist,
(23) The composition according to above item (22), which is an agent for the prevention and/or treatment of a cysLT$_1$/cysLT$_2$ receptor-mediated disease,
(24) The composition according to above item (23), wherein the cysLT$_1$/cysLT$_2$ receptor-mediated disease is a respiratory disease,
(25) The composition according to above item (24), wherein the respiratory disease is asthma, chronic obstructive pulmonary disease, pulmonary emphysema, chronic bronchitis, pneumonia, severe acute respiratory syndrome, acute respiratory distress syndrome, allergic rhinitis, sinusitis, pulmonary fibrosis or coughing,
(26) A medicine including the crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to any one of above items (1) to (6), the crystal of 4,4'-[2-methyl-7-({4-[4-(pentafluorophenyl)butoxy]phenyl}ethynyl)-1H-indole-1,3-diyl]dibutanoic acid according to any one of above items (7) to (12), or the crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to any one of above items (13) to (18) in combination with at least one selected from leukotriene receptor antagonists, steroid drugs, antihistamine drugs, phosphodiesterase inhibitors, elastase inhibitors, anticholinergic drugs, 5-lipoxygenase inhibitors, prostaglandins, non-steroid anti-inflammatory drugs, sympathomimetic drugs, thromboxane synthetase inhibitors, and thromboxane receptor antagonists,
(27) A method for preventing and/or treating a cysLT$_1$/cysLT$_2$ receptor-mediated disease in a mammal, including administrating an effective amount of the crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to any one of above items (1) to (6), the crystal of 4,4'-[2-methyl-7-({4-[4-(pentafluorophenyl)butoxy]phenyl}ethynyl)-1H-indole-1,3-diyl]dibutanoic acid according to any one of above items (7) to (12), or the crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to any one of above items (13) to (18) to the mammal,
(28) The crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to any one of above items (1) to (6), the crystal of 4,4'-[2-methyl-7-({4-[4-(pentafluorophenyl)butoxy]phenyl}ethynyl)-1H-indole-1,3-diyl]dibutanoic acid according to any one of above items (7) to (12), or the crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to any one of above items (13) to (18), for use as an agent for preventing and/or treating a cysLT$_1$/cysLT$_2$ receptor-mediated disease,
(29) Use of the crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to any one of above items (1) to (6), the crystal of 4,4'-[2-methyl-7-({4-[4-(pentafluorophenyl)butoxy]phenyl}ethynyl)-1H-indole-1,3-diyl]dibutanoic acid according to any one of above items (7) to (12), or the crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to any one of above items (13) to (18) for the manufacture of an agent for preventing and/or treating a cysLT$_1$/cysLT$_2$ receptor-mediated disease,
(30) The crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to any one of above items (1) to (6), produced by the steps of adding 4,4'-[4-fluoro-7-({4-[4-(3-fluoro-2-methylphenyl)butoxy]phenyl}ethynyl)-2-methyl-1H-indole-1,3-diyl]dibutanoic acid to a mixed solvent of acetone and water, then stirring the mixture at 50-60° C. for two hours or longer, and then cooling the mixture to form a precipitate,
(31) The crystal of 4,4'-[2-methyl-7-({4-[4-(pentafluorophenyl)butoxy]phenyl}ethynyl)-1H-indole-1,3-diyl]dibutanoic acid according to any one of above items (7) to (12), produced by the steps of dissolving 4,4'-[2-methyl-7-({4-[4-(pentafluorophenyl)butoxy]phenyl}ethynyl)-1H-indole-1,3-diyl]dibutanoic acid in a mixed solvent of ethanol and water at about 70° C., and then cooling the mixture to form a precipitate,
(32) The crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to any one of above items (13) to (18), produced by the steps of dissolving 4,4'-[4-fluoro-2-methyl-7-({4-[4-(2,3,4,6-tetrafluorophenyl)butoxy]phenyl}ethynyl)-1H-indole-1,3-diyl]dibutanoic acid in ethanol at about 65° C., and then adding the solution to water dropwise at inner temperature of 25° C. or lower,
(33) A method for producing the crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to any one of above items (1) to (6), including the steps of adding 4,4'-[4-fluoro-7-({4-[4-(3-fluoro-2-methylphenyl)butoxy]phenyl}ethynyl)-2-methyl-1H-indole-1,3-diyl]dibutanoic acid to a mixed solvent of acetone and water, then stirring the mixture at 50-60° C. for two hours or longer, and then cooling the mixture to form a precipitate,
(34) A method for producing the crystal of 4,4'-[2-methyl-7-({4-[4-(pentafluorophenyl)butoxy]phenyl}ethynyl)-1H-indole-1,3-diyl]dibutanoic acid according to any one of above items (7) to (12), including the steps of dissolving 4,4'-[2-methyl-7-({4-[4-(pentafluorophenyl)butoxy]phenyl}ethynyl)-1H-indole-1,3-diyl]dibutanoic acid in a mixed solvent of ethanol and water at about 70° C., and then cooling the mixture to form a precipitate, and
(35) A method for producing the crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to any one of above items (13) to (18), including the steps of dissolving 4,4'-[4-fluoro-2-methyl-7-({4-[4-(2,3,4,6-tetrafluorophenyl)butoxy]phenyl}ethynyl)-1H-indole-1,3-diyl]dibutanoic acid in ethanol at about 65° C., and then adding the solution to water dropwise at inner temperature of 25° C. or lower.

The Effect of the Invention

The crystalline form of the present invention is a compound having superior long-lasting effects in combination with a potent cysLT$_1$/cysLT$_2$ receptor antagonistic activity, and is therefore very useful as a long-acting agent for treating respiratory diseases, in case of oral administration.

Furthermore, the crystalline form of the present invention can be stably supplied in the production because of its thermodynamical stability, and has improved preservation stability due to improved photostability and humidity stability, and is therefore very useful as a bulk drug of a medicine.

MODE TO CARRY OUT THE INVENTION

In the present invention, compound I is a compound represented by the following structure:

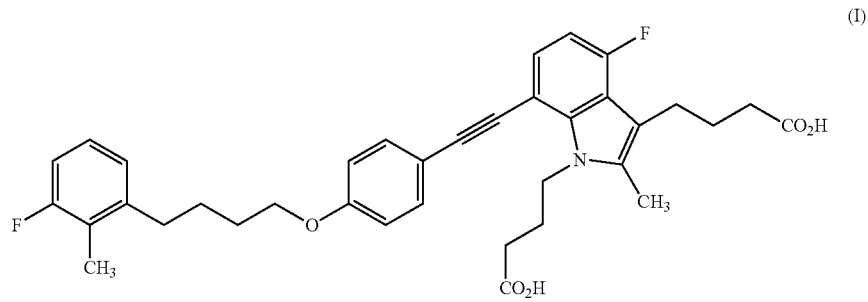 [SMILES: Cc1c(F)cccc1CCCCOc1ccc(C#Cc2ccc(F)c3c(CCCC(=O)O)c(C)n(CCCC(=O)O)c23)cc1]

(I)

In the present invention, compound I has three types of crystalline polymorph including type A crystal, type B crystal, and type C crystal. Of these, type A crystal is the crystalline form as described in Patent Document 3, while type B crystal and type C crystal are newly found crystalline forms in the present invention for the first time. The difference of the crystalline form is distinguished by, in particular, powdered X-ray diffraction spectrum and/or differential scanning calorimetry (DSC).

That is, type B crystal of compound I is characterized by at least one of physicochemical data (a) and (b) as follows. Preferably, it is characterized by both physicochemical data (a) and (b). (a) powdered X-ray diffraction spectrum shown in FIG. 1 or the diffraction angle (2θ) shown in Table 1, (b) differential scanning calorimetry (DSC) shown in FIG. 2, or having an endothermic peak of about 127° C.

Furthermore, type C crystal of compound I is characterized by at least one of physicochemical data (c) and (d) as follows. Preferably, it is characterized by both physicochemical data (c) and (d). (c) powdered X-ray diffraction spectrum shown in FIG. 3, the diffraction angle (2θ) shown in Table 2, or having peaks of about 7.29, 10.24, 12.15, 17.95, and 18.44 at 2θ degree in powdered X-ray diffraction spectrum, (d) differential scanning calorimetry (DSC) shown in FIG. 4, or having an endothermic peak of about 157° C.

Figure 3:
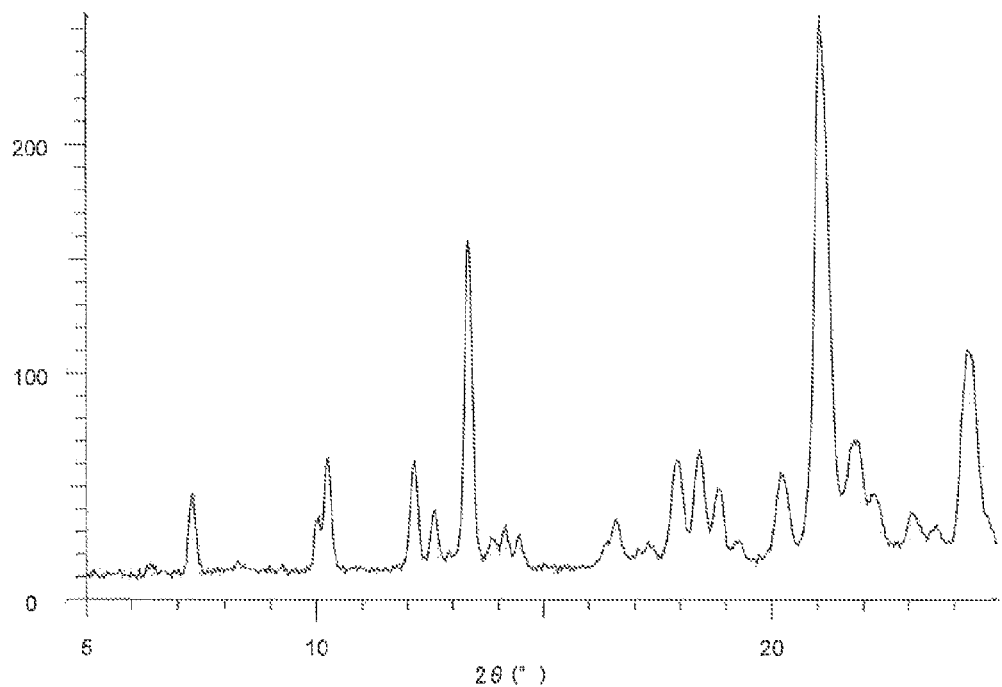
FIG. 3 shows a chart of powdered X-ray diffraction spectrum of type C crystal of 4,4'-[4-fluoro-7-({4-[4-(3-fluoro-2-methylphenyl)butoxy]phenyl}ethynyl)-2-methyl-1H-indole-1,3-diyl]dibutanoic acid.
Figure 4:
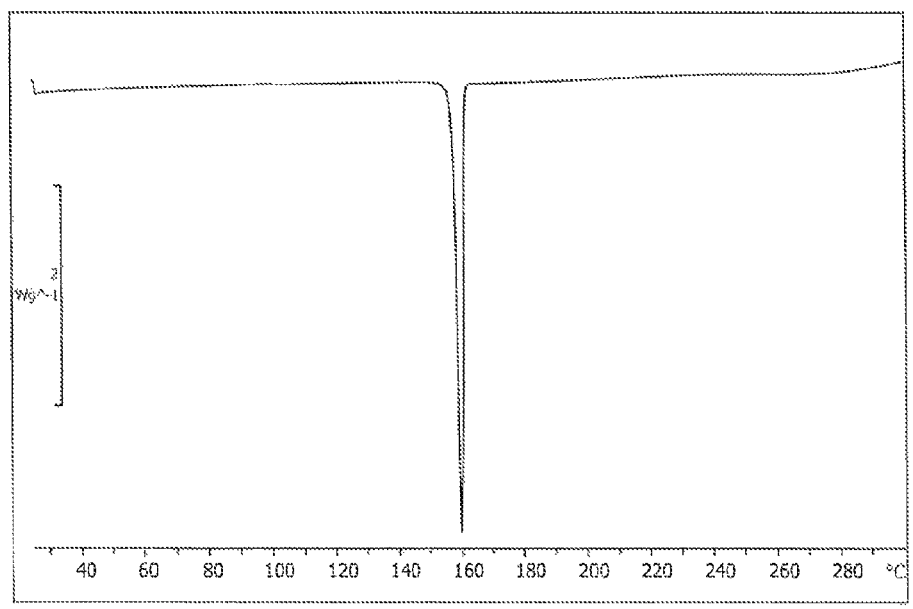
FIG. 4 shows a chart of differential scanning calorimetry (DSC) of type C crystal of 4,4'-[4-fluoro-7-({4-[4-(3-fluoro-2-methylphenyl)butoxy]phenyl}ethynyl)-2-methyl-1H-indole-1,3-diyl]dibutanoic acid.

Meanwhile, type A crystal of compound I as described in Patent Document 3 is characterized by FIG. 3 described therein (the chart of powdered X-ray diffraction spectrum), FIG. 4 described therein (the chart of differential scanning calorimetry (DSC)) and/or the diffraction angle (2θ) shown in Table 2 described therein. Also, it is characterized by powdered X-ray diffraction spectrum shown in FIG. 11 herein, or differential scanning calorimetry shown in FIG. 12 herein.

In the present invention, compound II is a compound represented by the following structure:

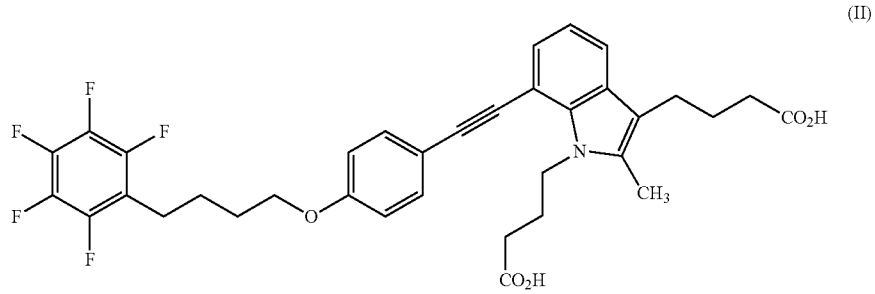 [SMILES: Cc1c(CCCC(=O)O)c2cccc(C#Cc3ccc(OCCCCc4c(F)c(F)c(F)c(F)c4F)cc3)c2n1CCCC(=O)O]

(II)

In the present invention, compound II has two types of crystalline polymorph including type A crystal and type B crystal. Of these, type A crystal is the crystalline form as described in Patent Document 3, while type B crystal is newly found crystalline form in the present invention for the first time. The difference of the crystalline form is distinguished by, in particular, powdered X-ray diffraction spectrum and/or differential scanning calorimetry (DSC).

That is, type B crystal of compound II is characterized by at least one of physicochemical data (e) and (f) as follows. Preferably, it is characterized by both physicochemical data (e) and (f). (e) powdered X-ray diffraction spectrum shown in FIG. 5, the diffraction angle (2θ) shown in Table 3, or having peaks of about 5.12, 10.16, 10.51, 14.90, and 20.42 at 2θ degree in powdered X-ray diffraction spectrum, (f) differential scanning calorimetry (DSC) shown in FIG. 6, or having an endothermic peak of about 146° C.

Figure 1:
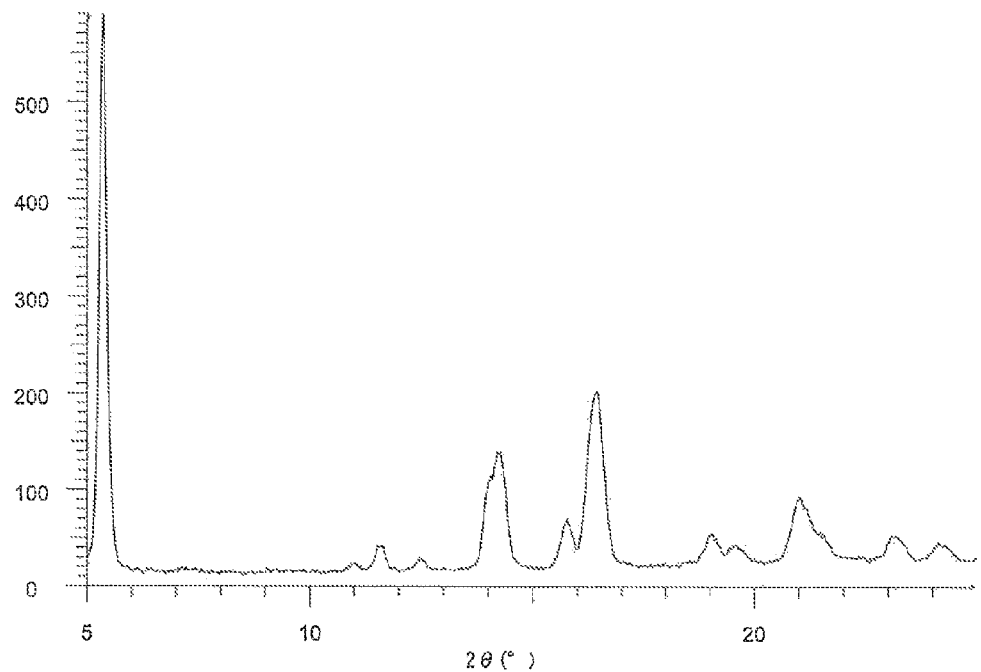
FIG. 1 shows a chart of powdered X-ray diffraction spectrum of type B crystal of 4,4'-[4-fluoro-7-({4-[4-(3-fluoro-2-methylphenyl)butoxy]phenyl}ethynyl)-2-methyl-1H-indole-1,3-diyl]dibutanoic acid.
Figure 2:
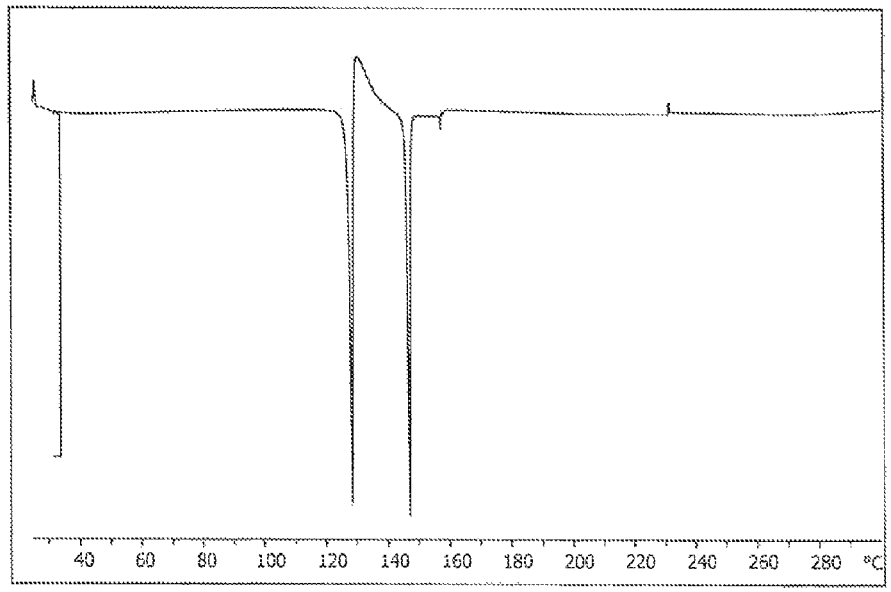
FIG. 2 shows a chart of differential scanning calorimetry (DSC) of type B crystal of 4,4'-[4-fluoro-7-({4-[4-(3-fluoro-2-methylphenyl)butoxy]phenyl}ethynyl)-2-methyl-1H-indole-1,3-diyl]dibutanoic acid.

Meanwhile, type A crystal of compound II as described in Patent Document 3 is characterized by FIG. 1 described therein (the chart of powdered X-ray diffraction spectrum), FIG. 2 described therein (the chart of differential scanning calorimetry (DSC)) and/or the diffraction angle (2θ) shown in Table 1 described therein. Also, it is characterized by powdered X-ray diffraction spectrum shown in FIG. 13 herein, or differential scanning calorimetry shown in FIG. 14 herein.

In the present invention, compound III is a compound represented by the following structure:

tal, and type C crystal. Of these, type A crystal is the crystalline form as described in Patent Document 3, while type B crystal and type C crystal are newly found crystalline forms in the present invention for the first time. The difference of the crystalline form is distinguished by, in particular, powdered X-ray diffraction spectrum and/or differential scanning calorimetry (DSC).

That is, type B crystal of compound III is characterized by at least one of physicochemical data (g) and (h) as follows. Preferably, it is characterized by both physicochemical data (g) and (h). (g) powdered X-ray diffraction spectrum shown in FIG. 7 or the diffraction angle (2θ) shown in Table 4, (h) differential scanning calorimetry (DSC) shown in FIG. 8, or having an endothermic peak of about 144° C.

Furthermore, type C crystal of compound III is characterized by at least one of physicochemical data (i) and (j) as follows. Preferably, it is characterized by both physicochemical data (i) and (j). (i) powdered X-ray diffraction spectrum shown in FIG. 9, the diffraction angle (2θ) shown in Table 5, or having peaks of about 5.25, 12.16, 15.08, 17.07, and 21.44 at 2θ degree in powdered X-ray diffraction spectrum, (j) differential scanning calorimetry (DSC) shown in FIG. 10, or having an endothermic peak of about 152° C.

Figure 5:
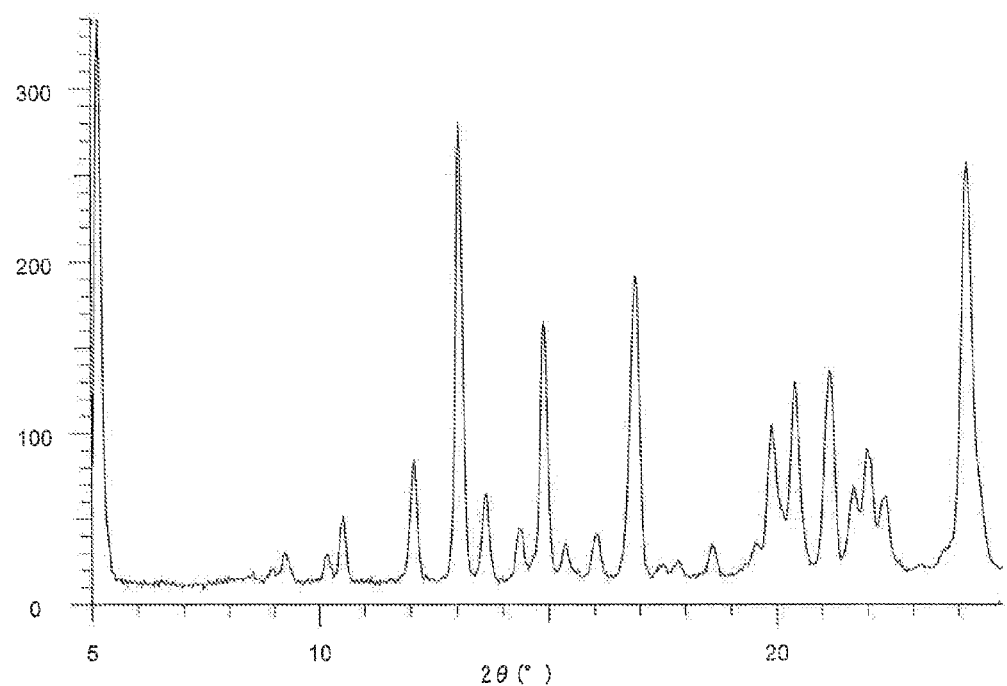
FIG. 5 shows a chart of powdered X-ray diffraction spectrum of type B crystal of 4,4'-[2-methyl-7-({4-[4-(pentafluorophenyl)butoxy]phenyl}ethynyl)-1H-indole-1,3-diyl]dibutanoic acid.
Figure 6:
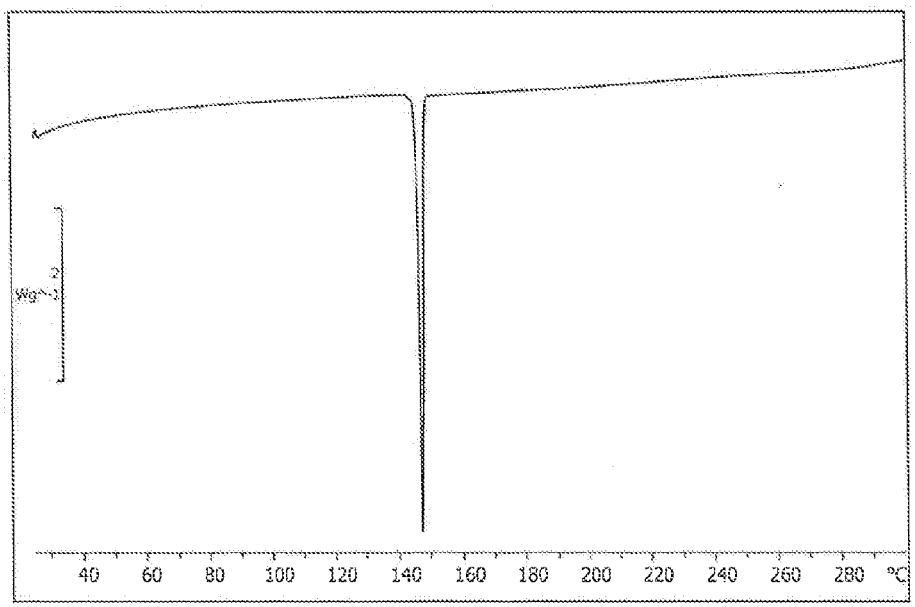
FIG. 6 shows a chart of differential scanning calorimetry (DSC) of type B crystal of 4,4'-[2-methyl-7-({4-[4-(pentafluorophenyl)butoxy]phenyl}ethynyl)-1H-indole-1,3-diyl]dibutanoic acid.

Meanwhile, type A crystal of compound III as described in Patent Document 3 is characterized by FIG. 5 described therein (the chart of powdered X-ray diffraction spectrum), FIG. 6 described therein (the chart of differential scanning calorimetry (DSC)) and/or the diffraction angle (2θ) shown in Table 3 described therein. Also, it is characterized by pow-

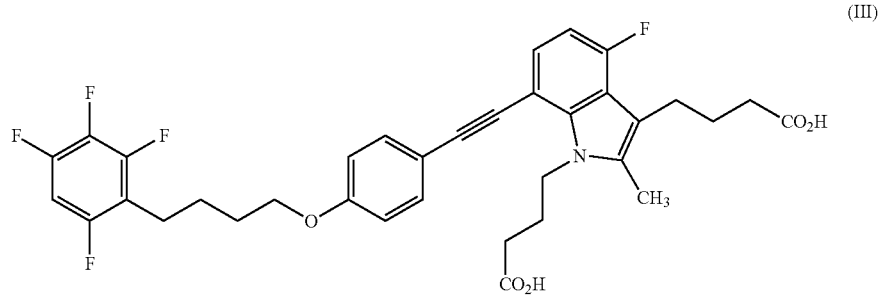 [SMILES: Cc1c(CCCC(=O)O)c2c(F)ccc(C#Cc3ccc(OCCCCc4c(F)cc(F)c(F)c4F)cc3)c2n1CCCC(=O)O]

(III)

Figure 15:
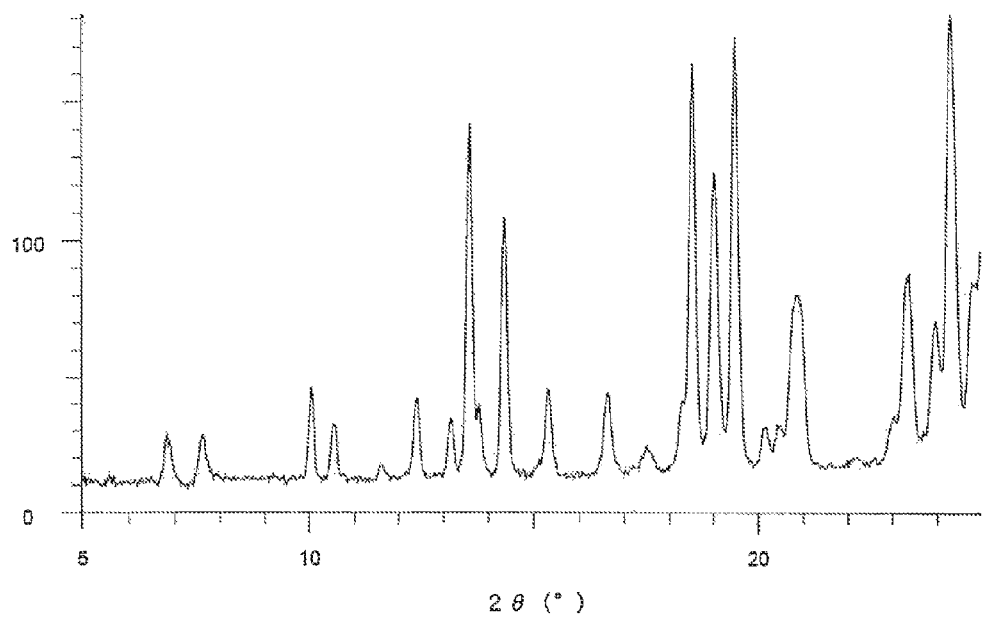
FIG. 15 shows a chart of powdered X-ray diffraction spectrum of type A crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid.
Figure 16:
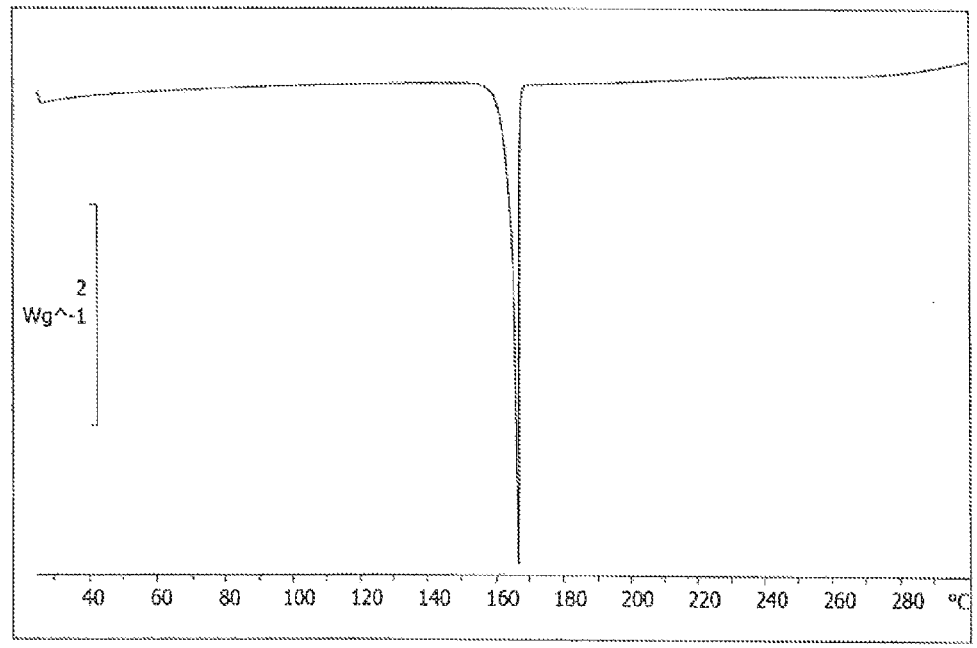
FIG. 16 shows a chart of differential scanning calorimetry (DSC) of type A crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid.

In the present invention, compound III has three types of crystalline polymorph including type A crystal, type B crysdered X-ray diffraction spectrum shown in FIG. 15 herein, or differential scanning calorimetry shown in FIG. 16 herein.

In the present invention, each crystalline form of compound I, compound II and compound III is defined by physicochemical data as described herein. However, each spectrum data are somewhat variable in nature, and they should not be construed strictly.

For example, in the powdered X-ray diffraction spectrum data, the diffraction angle (2θ) and their overall patterns are important in nature for identification of the identity of crystals, and the relative intensity is somewhat variable depending on direction of crystal growth, size of particle, and the condition of measurement.

Also, in differential scanning calorimetry (DSC) in confirming the identity of crystals, the overall patterns are important but somewhat variable depending on the condition of measurement.

Therefore, in the crystalline form of the present invention, a crystal form in which powdered X-ray diffraction spectrum or differential scanning calorimetry (DSC) and their pattern are similar totally are within the crystalline form of the present invention.

In the present invention, the compound shown by general formula (I) including compound I, compound II, and compound III can be produced according to any known method, for example, a method shown as follows, and its similar method or Examples.

It is noted that in the present invention, "dioxane" means 1,4-dioxane, and "dimethoxyethane" means 1,2-dimethoxyethane.

The compound shown by general formula (I) including compound I, compound II, and compound III

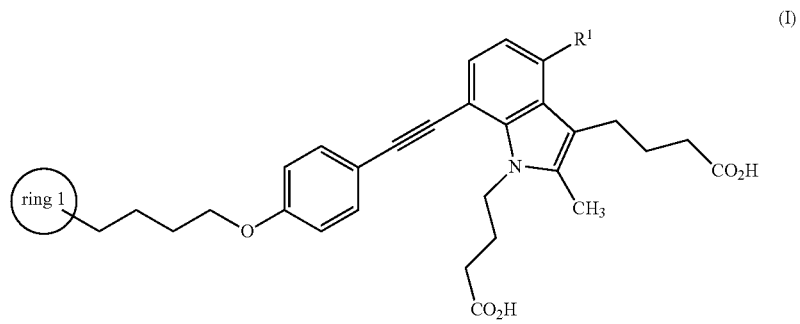
(I)

wherein ring 1 represents

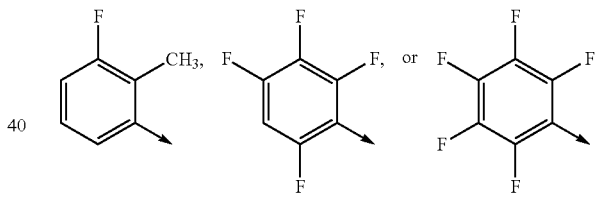

$R^1$ represents a hydrogen atom, or a fluorine atom, can be produced by any known method, for example, the method shown as follows, and its similar method or any method shown in Examples.

The compound shown by general formula (I) can be produced by alkaline hydrolysis reaction of a compound shown by general formula (II)

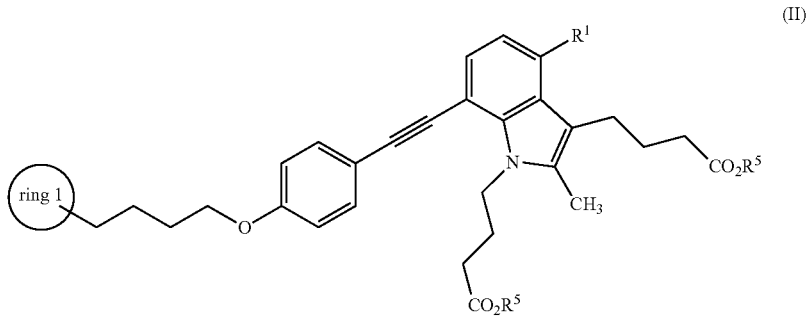
(II)

wherein R[5] represents a C1-6 alkyl group (preferably, a methyl group, an ethyl group), the other symbols represent the same meaning as described above.

The alkaline hydrolysis reaction of the compound shown by general formula (II) is carried out, for example, by using a hydroxide of alkali metals (sodium hydroxide, potassium hydroxide, lithium hydroxide, etc.), a hydroxide of alkaline earth metals (barium hydroxide, calcium hydroxide, etc.) or a carbonate of alkali metals and alkaline earth metals (sodium carbonate, potassium carbonate, etc.), or an aqueous solution thereof or a mixture thereof in an organic solvent (ethylene glycol, methanol, ethanol, 2-propanol, tetrahydrofuran, dioxane, dimethoxyethane, diglyme, etc.) at a temperature of 0 to 120° C. Preferably, the reaction is carried out by reacting with an aqueous solution of sodium hydroxide or potassium hydroxide in a mixed organic solvent of methanol or ethanol and tetrahydrofuran or dimethoxyethane at about 25-50° C.

The compound of formula (II) can be prepared according to the method as shown in Reaction Scheme 1. In Reaction Scheme 1, X represents a bromine atom, an iodine atom, or a trifluoromethanesulfonyloxy group (preferably, a bromine atom), Z represents a halogen atom, a hydroxy group, a methanesulfonyloxy group, or a p-toluenesulfonyloxy group (preferably, a halogen atom), and other symbols represent the same meaning as defined above.

Reaction Scheme

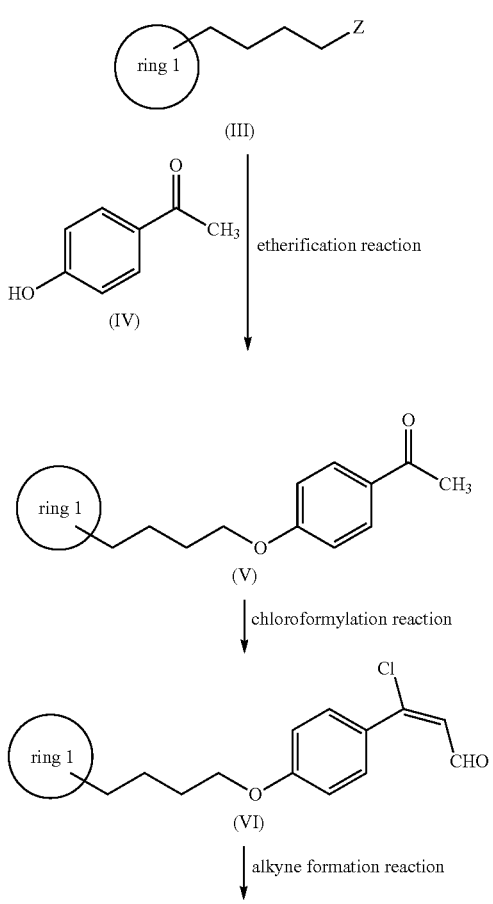

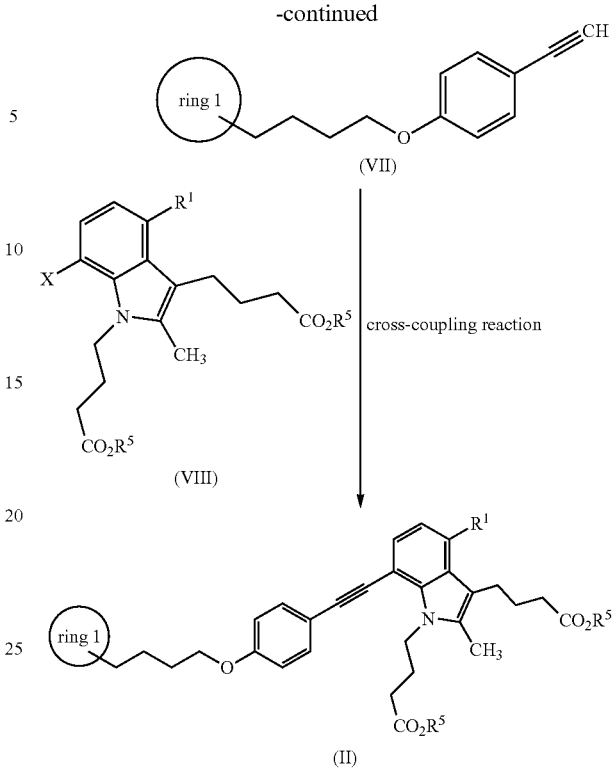

In Reaction Scheme 1, etherification reaction, chloroformylation reaction, alkyne formation reaction, and cross-coupling reaction may be carried out under any known conditions, for example, under conditions as set forth below, or under conditions of Examples as described in the present specification.

(1) When Z is a halogen atom, a methanesulfonyloxy group, or a p-toluenesulfonyloxy group, the etherification reaction between the compound of formula (III) and the compound of formula (IV) is carried out, for example, by reacting in an organic solvent (such as dimethylformamide, dimethylsulfoxide, N,N-dimethylacetamide, N-methyl-2-pyrrolidinone, 1,3-dimethyl-2-imidazolidinone, chloroform, methylene chloride, diethylether, tetrahydrofuran, acetone, benzene, or toluene), in the presence of a hydroxide of alkali metals (such as sodium hydroxide, potassium hydroxide, or lithium hydroxide), a hydroxide of alkaline earth metals (such as barium hydroxide, or calcium hydroxide) or a carbonate of alkali metals (such as sodium carbonate, potassium carbonate, or cesium carbonate), a phosphate of alkali metals (such as potassium phosphate), or an aqueous solution thereof or a mixture thereof, and in the presence or absence of a phase-transfer catalyst (such as tetrabutylammonium chloride, tetrabutylammonium bromide, tetrabutylammonium iodide, tetrabutylammonium acetate, tetrabutylammonium hydroxide, tetrabutylammonium hydrogen sulfide, benzyltrimethyl ammonium chloride), a halide of alkali metals (such as potassium iodide, sodium iodide, potassium bromide, sodium bromide) at a temperature of 0° C. to 120° C. Preferably, the reaction is carried out by reacting the compound in the presence of potassium carbonate, potassium phosphate, or cesium carbonate and in the presence or absence of aqueous potassium iodide solution in N-methyl-2-pyrrolidinone, dimethylformamide, dimethylsulfoxide, or N,N-dimethylacetamide at about 40-80° C. (2) When Z is a hydroxy group, the etherification reaction is carried out, for example, by reacting in an organic solvent (such as dichloromethane, diethylether, tetrahydrofuran, acetonitrile, benzene, or toluene), in the presence of an azo compound (such as diethyl azodicarboxylate, diisopropyl azodicarboxylate, 1,1'-(azodicarbonyl)dipiperidine, or 1,1'-azobis(N,N-dimethylformamide)) and a phosphine compound (such as triphenylphosphine, tributylphosphine, or trimethylphosphine), at a temperature of 0 to 60° C.

In Reaction Scheme 1, the chloroformylation reaction of the compound of general formula (V) is carried out, for example, by reacting with a chlorinating agent (such as phosphoryl chloride, phosphorous pentachloride, thionyl chloride, phosphorous trichloride) in a formylating agent (such as N,N-dimethylformamide, N-formylpyrrolidine, N-formylpiperidine, N-methylformanilide, N-formylmorpholine, N-formyldiphenylamine, N-formyldiethylamine, N-formyldiisopropylamine), or in combination of these formylating agents and an organic solvent (such as benzene, toluene, xylene, chlorobenzene, o-dichlorobenzene, chloroform, methylene chloride, ethylene dichloride, diethyl ether, dimethoxyethane, acetonitrile, nitromethane, nitroethane) at 0-120° C. Preferably, the reaction is carried out by reacting with phosphoryl chloride in N,N-dimethylformamide at about 25° C.

In Reaction Scheme 1, the alkyne formation reaction of the compound of general formula (VI) is carried out, for example, by reacting the compound in an organic solvent (such as dimethylsulfoxide, N,N-dimethylformamide, N,N-dimethylacetamide, N-methyl-2-pyrrolidinone, 1,3-dimethyl-2-imidazolidinone, methylene chloride, diethyl ether, t-butylmethylether, tetrahydrofuran, dioxane, dimethoxyethane, diglyme, benzene, toluene, ethylene glycol, methanol, ethanol, 2-propanol), in the presence of a hydroxide of alkali metals (such as sodium hydroxide, potassium hydroxide, lithium hydroxide), an alkoxide of alkali metals (such as sodium methoxide, sodium ethoxide, sodium t-butoxide, potassium t-butoxide), a hydroxide of alkaline earth metals (such as barium hydroxide, calcium hydroxide), or carbonate thereof (such as sodium carbonate, potassium carbonate, cesium carbonate), a phosphate of alkali metals (such as potassium phosphate), or the aqueous solution or mixture thereof, in the presence or absence of a phase transfer catalyst (such as tetrabutylammonium chloride, tetrabutylammonium bromide, tetrabutylammonium iodide, tetrabutylammonium acetate, tetrabutylammonium hydroxide, tetrabutyl ammonium hydrogensulfate, benzyltrimethylammonium chloride) at 0-100° C. Preferably, the reaction is carried out by reacting the compound with aqueous solution of potassium hydroxide or sodium hydroxide in dimethylsulfoxide or dioxane at about 50-70° C.

Cross-coupling reaction of the compound shown by general formula (VII) and the compound shown by general formula (VIII) is carried out, for example, by reacting in an organic solvent (such as ethyl acetate, isopropyl acetate, benzene, toluene, xylene, heptane, cyclohexane, tetrahydrofuran, dioxane, dimethoxyethane, ethanol, 2-propanol, polyethylene glycol, dimethylsulfoxide, N,N-dimethylformamide, N,N-dimethylacetamide, N-methyl-2-pyrrolidinone, methylene chloride, chloroform, acetone, acetonitrile, water, or a mixture thereof) or under solvent-free condition, in the presence or absence of a base (such as diethylamine, triethylamine, propylamine, diisopropylamine, diisopropylethylamine, dibutylamine, tributylamine, pyrrolidine, piperidine, N-methylpiperidine, 1,4-diazabicyclo[2.2.2]octane (DABCO), pyridine, sodium hydroxide, sodium hydrogen carbonate, sodium carbonate, potassium carbonate, cesium carbonate, sodium phosphate, potassium phosphate, potassium fluoride) and a catalyst (such as palladium catalyst (for example, tetrakis(triphenylphosphine)palladium (Pd(PPh$_3$)$_4$), dichlorobis(triphenylphosphine)palladium (PdCl$_2$(PPh$_3$)$_2$), palladium acetate (Pd(OAc)$_2$), palladium dichloride (PdCl$_2$), palladium black, bis{1,1'-bis(diphenylphosphino)ferrocene}dichloropalladium (PdCl$_2$(dppf)$_2$), dichlorobisallyl palladium (Pd$_2$Cl$_2$(allyl)$_2$), palladium phenylbis(triphenylphosphine) iodide (PhPdI(PPh$_3$)$_2$), tris(dibenzylideneacetone)dipalladium (Pd$_2$(dba)$_3$), bis(tri-tert-butylphosphine)palladium (Pd($^t$Bu$_3$P)$_2$)) alone, or a mixture thereof with a ligand (such as triphenylphosphine, tri-tert-butylphosphine), or a mixture thereof with a copper catalyst (e.g. copper (I) iodide), and in the presence or absence of a phase-transfer catalyst (such as tetrabutylammonium chloride, tetrabutylammonium bromide, tetrabutylammonium iodide, tetrabutylammonium acetate) at a temperature of room temperature to 120° C. Preferably, the reaction is carried out by reacting in ethyl acetate, isopropyl acetate, tetrahydrofuran or acetonitrile or under solvent-free condition, using triethylamine or diisopropylamine and a catalyst (bis(triphenylphosphine)palladium dichloride (PdCl$_2$(PPh$_3$)$_2$) or bis(tri-t-butylphosphine)palladium (Pd($^t$Bu$_3$P)$_2$) alone, or a mixture thereof with triphenylphosphine, or a mixture thereof with copper (I) iodide at about 60-85° C.

The compounds which are used as starting materials or reagents and of the formulae (III) and (IV) are known per se or can be easily prepared by using the methods described in Examples of the present specification, or any conventional known method, for example, any method described in "Comprehensive Organic Transformations: A Guide to Functional Group Preparations, 2nd Edition (written by Richard C. Larock, John Wiley & Sons Inc., 1999)".

The compound of the formula (VIII) can be prepared according to the method as shown in Reaction Scheme 2. In Reaction Scheme 2, $R^2$ represents a C1-6 alkyl group or a hydrogen atom (preferably, represents an ethyl group, a butyl group), $R^3$ represents a C1-6 alkyl group or a hydrogen atom (preferably, an ethyl group, a butyl group), $R^4$ represents a halogen atom (preferably, a bromide atom), and other symbols represent the same meaning as defined above.

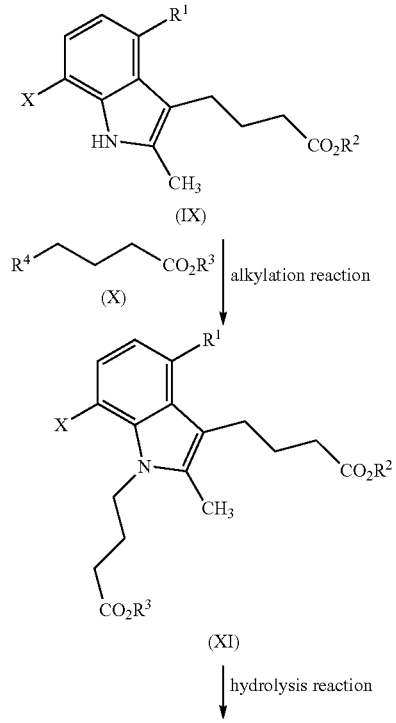

Reaction Scheme 2

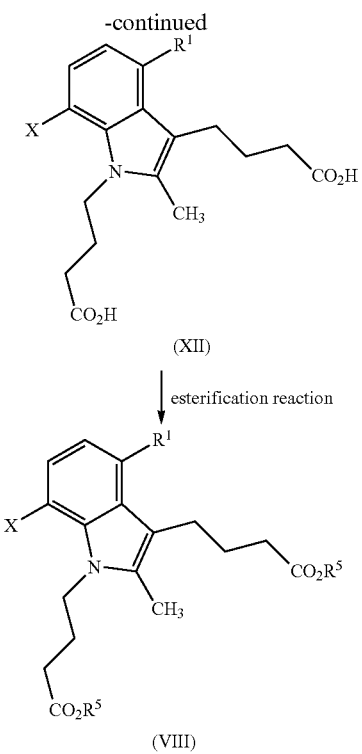

(XII)

↓ esterification reaction (VIII)

In Reaction Scheme 2, the alkylation reaction, the hydrolysis reaction and the esterification reaction may be carried out under known conditions, for example, under conditions as set forth below, or under conditions of Examples as described in the present specification.

In Reaction Scheme 2, the alkylation reaction of the compound shown by general formula (IX) is carried out, for example, by reacting a phosphate of alkali metals (such as sodium phosphate, potassium phosphate), a carbonate of alkali metals (such as sodium carbonate, potassium carbonate, cesium carbonate), an alkoxide of alkali metals (such as sodium methoxide, sodium ethoxide, sodium t-butoxide, potassium t-butoxide), a hydroxide of alkali metals (such as sodium hydroxide, potassium hydroxide, lithium hydroxide) or a hydroxide of alkaline earth metals (such as barium hydroxide, calcium hydroxide) and 4-halobutyrate ester of general formula (X) in the presence or absence of a phase transfer catalyst (such as tetrabutylammonium chloride, tetrabutylammonium bromide, tetrabutylammonium iodide, tetrabutylammonium acetate, tetrabutylammonium hydroxide, tetrabutyl ammonium hydrogensulfate) in an organic solvent (such as dimethylsulfoxide, N,N-dimethylformamide, N,N-dimethylacetamide, N-methyl-2-pyrrolidinone, 1,3-dimethyl-2-imidazolidinone, methylene chloride, diethyl ether, t-butyl methyl ether, tetrahydrofuran, acetone, diglyme, benzene, toluene) at 0-100° C. Preferably, in N,N-dimethylacetamide, dimethylsulfoxide, N,N-dimethylformamide, N-methyl-2-pyrrolidinone or 1,3-dimethyl-2-imidazolidinone, the reaction is carried out by reacting potassium phosphate or cesium carbonate and ethyl 4-bromobutyrate at about 45-60° C.

In Reaction Scheme 2, the hydrolysis reaction of the compound shown by general formula (XI) is carried out, for example, by reacting an aqueous solution of alkali metal hydroxides (such as sodium hydroxide, potassium hydroxide, lithium hydroxide), an aqueous solution of alkalline earth metal hydroxides (such as barium hydroxide, calcium hydroxide) in an organic solvent (such as methanol, ethanol, 2-propanol, ethylene glycol, diethyl ether, t-butyl methyl ether, tetrahydrofuran, dioxane, dimethoxyethane, diglyme) at 0-100° C. Preferably, the reaction is carried out by reacting with an aqueous solution of sodium hydroxide or potassium hydroxide in a mixed organic solvent of methanol or ethanol and tetrahydrofuran or dimethoxyethane at about 25-50° C.

In Reaction Scheme 2, the esterification reaction of the compound shown by general formula (XII) is carried out, for example, by reacting an organic acid (such as sulfuric acid, hydrochloric acid, methanesulfonic acid, p-toluene sulfonic acid), or solid acid (amberite etc.) in an organic solvent (such as methanol) at 0-65° C. Preferably, the reaction is carried out by reacting with sulfuric acid in methanol at 50° C.

As an alternative method, the reaction is carried out by reacting a methylating agent (such as methyl iodide, dimethyl sulfate) and a carbonate of alkali metals and alkaline earth metals (such as sodium carbonate, potassium carbonate, cesium carbonate) in an organic solvent (such as dimethylsulfoxide, N,N-dimethylformamide, N,N-dimethylacetamide, N-methyl-2-pyrrolidinone, 1,3-dimethyl-2-imidazolidinone, acetone, tetrahydrofuran, dioxane, dimethoxyethane, diglyme) at 0-100° C.

The compounds which are used as starting materials or reagents and of general formulae (IX) and (X) are known per se or can be easily prepared by using the methods described in Examples of the present specification, or any conventional known method, for example, methods described in "Comprehensive Organic Transformations: A Guide to Functional Group Preparations, 2nd Edition (written by Richard C. Larock, John Wiley & Sons Inc., 1999)".

In each reaction in the present specification, as will be apparent to those skilled in the art, the reaction with heating may be carried out using a water bath, an oil bath, a sand bath, or microwave.

In each reaction in the present specification, a solid phase-supported reagent which is appropriately supported on a polymer (for example, polystyrene, polyacrylamide, polypropylene, polyethylene glycol) may also be used.

In each reaction in the present specification, the reaction product can be purified by conventional purification means, for example, distillation under normal pressure or reduced pressure, high performance liquid chromatography using a silica gel or magnesium silicate, thin layer chromatography, ion-exchange resin, scavenger resin or column chromatography or washing, or recrystallization. The purification may be carried out for every reaction, or may be carried out after the completion of some reactions.

In the present invention, the crystalline form of the present invention can be prepared according to any known method, for example, a method shown as follows, and its similar method or Examples. Also, when re-precipitated, seed crystal may be used or not.

Type C crystal of compound I can be prepared from compound I produced by similar to Example 14(2) of Patent Document 3, or Example 10(1) described below, for example, using the following method.

Compound I is added to a mixed solvent of acetone and water and stirred at about 70° C. for 8 hours or longer. Then, type C crystal of compound I can be obtained by cooling to room temperature.

Alternatively, compound I is added to a mixed solvent of acetone and water and the seed crystal is added, and stirred at about 50-60° C. for 2 hours or longer. Then, type C crystal of compound I can be obtained by cooling to room temperature.

The method for obtaining type C crystal of compound I is preferably the following method.

Compound I is added to a mixed solvent of acetone and water and the seed crystal is added, and stirred at 50-60° C. for 2 hours or longer. Then the compound is cooled to room temperature.

Type B crystal of compound II can be prepared from the compound produced by similar to Example 9 of Patent Document 3, or Example 9 described below, for example, using the following method.

Compound II can be resolved in a mixed solvent (for example, a mixed solvent of ethanol, acetonitrile, 1-propanol or 2-propanol and water, a mixed solvent of acetonitrile or t-butyl methyl ether and octane), and then be cooled to obtain type B crystal of compound II.

The method for obtaining type B crystal of compound II is preferably the following method.

Compound II is resolved in a mixed solvent of ethanol and water at about 70° C. Then the compound is cooled to room temperature.

Type C crystal of compound III can be prepared from the compound produced by similar to Example 14(3) of Patent Document 3, or Example 10(2) described below, for example, using the following method.

Type C crystal of compound III can be obtained by dissolving compound III in ethanol at about 65° C., and then adding this solution to water at inner temperature of 25° C. or lower.

[Toxicity]

Type C crystal of compound I, type B crystal of compound II, or type C crystal of compound III has a very low toxicity and is considered to be safe enough for pharmaceutical use.

[Application to Pharmaceuticals]

The crystalline form of the present invention is intended to antagonize the $cysLT_1/cysLT_2$ receptor. Accordingly, the compound is useful as, for example, airway contraction inhibitors, inflammatory cell (for example, eosinophils, neutrophils, lymphocytes, basophils, etc.) infiltration inhibitors, mucus secretion inhibitors, or inhibitors of increased airway hypersensitivity.

Furthermore, the crystalline form of the present invention is useful as an agent for preventing and/or treating for $cysLT_1/cysLT_2$ receptor-associated diseases, for example, respiratory diseases (for example, asthma (bronchial asthma, aspirin-induced asthma, exercise-induced asthma, etc.), chronic obstructive pulmonary diseases (COPD), pulmonary emphysema, chronic bronchitis, pneumonia (interstitial pneumonia, eosinophilic pneumonia, etc.), severe acute respiratory syndrome (SARS), acute respiratory distress syndrome (ARDS), apnea syndrome (sleep apnea syndrome, sleep-disordered breathing accompanied by adenotonsillar hypertrophy, sleep-disordered breathing after adenoidectomy/tonsillectomy, or the like), allergic rhinitis, sinusitis (acute sinusitis, chronic sinusitis, eosinophilic sinusitis etc.), pulmonary fibrosis, coughing (chronic coughing, dry coughing, etc.), and the like), or as an expectorant agent or an antitussive agent.

In addition, the crystalline form of the present invention is also useful as an agent for the improvement of respiratory function. As used herein, the term "respiratory function" refers to, for example, inflow or outflow of air into/from the lung (pulmonary vital capacity), delivery of oxygen from the lung to the blood to result in discharge of $CO_2$ from the blood to the outside of the body (oxygen exchange capacity), respiratory resistance, or the like.

As used herein, the term "respiratory organ" refers to a body part which is involved in respiration, such as airway, oral cavity, nasal cavity, nasal sinuses, trachea, bronchi, bronchiole, and lung.

In addition, the crystalline form of the present invention is also useful for preventing and/or treating other diseases in which the $cysLT_1/cysLT_2$ receptor is involved, such as cardiovascular diseases (for example, ischemic heart disease (angina pectoris, myocardial infarction), acute coronary syndromes, cardiac insufficiency, arrhythmia, cardiomyopathy (dilated cardiomyopathy, hypertrophic cardiomyopathy, etc.), pericarditis, valvulitis, myocarditis, cardiac tamponade, low cardiac output syndrome, mitral stenosis, etc.), pulmonary hypertension (primary pulmonary hypertension), cystic fibrosis, atherosclerosis, pulmonary fibrosis, stroke (cerebral infarction), cerebral edema, interstitial cystitis, aneurysm, headache (migraine, cluster headache, tension-type headache, etc.), gynecological diseases (endometriosis, dysmenorrhea, etc.), Meniere's disease, epilepsy, cancer, renal diseases, gastrointestinal ulceration, inflammatory bowel disease, exanthem, aging macular degeneration, diabetic retinopathy and the like.

Furthermore, the crystalline form of the present invention can be supplied in the production because of its thermodynamical stability, and has improved preservation stability due to improved photostability and humidity stability, and is therefore very useful as a bulk drug of a medicine.

As used herein, the term "$cysLT_1/cysLT_2$ receptor antagonistic activity" means that the compound of the present invention exhibits antagonistic effects on both of the $cysLT_1$ receptor and the $cysLT_2$ receptor.

The crystalline form of the present invention may be administered in combination with other medicaments so as to (1) supplement and/or enhance the preventive and/or treatment effects of the crystalline form of the present invention, (2) improve the pharmacokinetics and absorption of the crystalline form of the present invention and decrease the dosage of the crystalline form of the present invention, and/or (3) decrease adverse effects of the crystalline form of the present invention.

The crystalline form of the present invention and the other medicaments may be administered in the form of a combination drug having these components formulated into one preparation or may be administered in separate preparations. In the case where these medicaments are administered in separate preparations, they may be administered simultaneously or at different times. In the latter case, the crystalline form of the present invention may be administered before the other medicaments. Alternatively, the other medicaments may be administered before the crystalline form of the present invention. The method for the administration of these may be the same or different.

The above-mentioned other medicaments may be either low-molecular compounds or high-molecular proteins, polypeptides, polynucleotides (DNAs, RNAs, and genes), antisenses, decoys, antibodies, vaccines, etc. The dose of the other medicaments may be appropriately selected taking the clinically used dose as a standard. The formulation ratio between the crystalline form of the present invention and the other medicaments may be appropriately selected, depending on the age and body weight of a subject to be treated, the method and time of administration, the disease to be targeted, its symptoms or conditions, the combination, etc. For example, the other medicaments may be used in a range of 0.01 to 100 parts by mass, relative to 1 part by mass of the crystalline form of the present invention. The other medicaments may be administered alone or in any combination thereof, for example, any one or more compounds selected from the following same or different groups at appropriate ratios. The other medicaments which serve to supplement and/or enhance the preventive and/or treatment effects of the crystalline form of the present invention are understood to encompass not only the ones which have ever been discovered, but also the ones to be discovered in the future, on the basis of the above-mentioned mechanism.

The diseases on which the above-described combination drug is effective in terms of preventive and/or treatment effects are not specifically limited. The diseases may be those in which the preventive and/or treatment effects of the crystalline form of the present invention are supplemented and/or enhanced.

Examples of the other medicaments, which act to supplement and/or enhance the preventive and/or treatment effects of the crystalline form of the present invention against asthma, include leukotriene receptor antagonists, antihistamine agents, phosphodiesterase inhibitors, elastase inhibitors, anticholinergic agents, antiallergic agents (chemical mediator release inhibitors, histamine antagonists, thromboxane synthase inhibitors, thromboxane receptor antagonists, Th2 cytokine inhibitors, etc.), steroidal agents, bronchodilating agents (xanthine derivatives, sympathomimetic agents, parasympatholytic agents), vaccine therapy agents, gold formulations, Chinese herbal medicines, non-steroidal anti-inflammatory agents, 5-lipoxygenase inhibitors, 5-lipoxygenase activating protein antagonists, leukotriene synthesis inhibitors, prostaglandins, cannabinoid-2 receptor stimulants, antitussive agents, expectorant agents, extracts from cutaneous tissue of rabbit inoculated with vaccinia virus, and the like.

Examples of the leukotriene receptor antagonist include pranlukast hydrate, montelukast sodium, zafirlukast, MK-571, LY-203647, WY-46016, WY-48422, WY-49353, WY-49451, RG-12553, MDL-43291, CGP-44044A, RG-14524, LY-287192, LY-290324, L-695499, RPR-105735B, WAY-125007, OT-4003, LM-1376, LY-290154, SR-2566, L-740515, LM-1453, CP-195494, LM-1484, CR-3465, ablukast, pobilukast, sulukast, L-648051, RG-12525, RG-7152, SK&F-106203, SR-2640, WY-50295, iralukast sodium, verlukast, MCC-847, BAY-x-7195, ritolukast, cinalukast, CGP-44826, FK-011, YM-158, MEN-91507, KCA-757, RS-601, RS-635, S-36496, ZD-3523, DS-4574, pirodomast, AS-35, YM-57158, MC1826, NZ-107, 4414-CERM, YM-16638, Wy-48252, Wy-44329, Wy-48090, VUF-4679, tomelukast, SM-11044, SC-39070, OT-3473, N-2401, LY-243364, L-649923, doqualast, DP-1934, YM-17551, Wy-47120, VUF-K-8707, SK&F-88046, SK&F-101132, SK&F-102922, LY-137617, LY-163443, LY-302905, L-647438, L-708738, KY-234, FPL-55712, CP-288886, S-36527, CGP-35949, CS-615, MDL-19301D, SCH-40120, and ZD-3705, etc.

It is preferable that the leukotriene receptor antagonist is pranlukast hydrate, montelukast sodium, zafirlukast or MK-571, and it is more preferable that the leukotriene receptor antagonist is pranlukast hydrate, montelukast sodium or zafirlukast.

Examples of the antihistamine agent include diphenhydramine, diphenylpyraline hydrochloride, diphenylpyraline teoclate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andolast, auranofin, acrivastine, etc.

A phosphodiesterase 4 inhibitor is preferable as the phosphodiesterase inhibitor. Examples of the phosphodiesterase 4 inhibitor include rolipram, cilomilast (trade name: Ariflo), Bay19-8004, NIK-616, roflumilast (BY-217), cipamfylline (BRL-61063), atizoram (CP-80633), SCH-351591, YM-976, V-11294A, PD-168787, D-4396, IC-485, etc.

Examples of the elastase inhibitor include sivelestat sodium hydrate (ONO-5046), ONO-6818, MR-889, PBI-1101, EPI-HNE-4, R-665, ZD-0892, ZD-8321, GW-311616, AE-3763, DMP-777, L-659286, L-658758, L-680833, L-683845, etc.

Examples of the anticholinergic agent include ipratropium bromide, oxitropium bromide, flutropium bromide, cimetropium bromide, temiverine, tiotropium bromide, revatropate (UK-112166), etc.

Among the antiallergic agents, examples of the chemical mediator release inhibitor include sodium cromoglycate, tranilast, amlexanox, repirinast, ibudilast, pemirolast potassium, tazanolast, nedocromil, cromoglycate, israpafant, etc.

Among the antiallergic agents, examples of the histamine antagonist include ketotifen fumarate, azelastine hydrochloride, oxatomide, mequitazine, terfenadine, emedastine difumarate, epinastine hydrochloride, ebastin, cetirizine hydrochloride, olopatadine hydrochloride, loratadine, fexofenadine, etc.

Among the antiallergic agents, examples of the thromboxane synthase inhibitor include ozagrel hydrochloride, imitrodast sodium, etc.

Among the antiallergic agents, examples of the thromboxane antagonist include seratrodast, ramatroban, domitroban calcium hydrate, KT-2-962, etc.

Among the antiallergic agents, examples of the Th2 cytokine inhibitor include suplatast tosilate, etc.

Steroidal agents as external medicines include clobetasol propionate, diflorasone acetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone dipropionate, triamcinolone acetonide, flumethasone pivalate, alclometasone dipropionate, clobetasone butyrate, prednisolone, fludroxycortide, etc.

Steroidal agents as internal medicines and injections include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyl acetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone, etc. Inhalant medicines include beclometasone dipropionate, fluticasone propionate, budesonide, flunisolide, triamcinolone, ST-126P, ciclesonide, dexamethasone palomithioate, mometasone furoate, prasterone sulfonate, deflazacort, methylprednisolone suleptanate, methylprednisolone sodium succinate, etc.

Among the bronchodilating agents, examples of the xanthine derivative include aminophylline, theophylline, doxophylline, cipamfylline, diprophylline, proxyphylline, choline theophylline, etc.

Among the bronchodilating agents, examples of the sympathomimetic agent include epinephrine, ephedrine hydrochloride, dl-methylephedrine hydrochloride, methoxyphenamine hydrochloride, isoproterenol sulfate, isoproterenol hydrochloride, orciprenaline sulfate, clorprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromide, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KUR-1246, KUL-7211, AR-C89855, S-1319, etc.

Among the bronchodilating agents, examples of the parasympatholytic agent include ipratropium bromide, flutropium bromide, oxitropium bromide, cimetropium bromide, temiverine, tiotropium bromide, revatropate (UK-112166), etc.

Examples of the vaccine therapy agent include paspat, asthremedin, broncasma berna, CS-560, etc.

Examples of the gold formulation include sodium aurothiomalate, etc.

Examples of the basic non-steroidal anti-inflammatory agent include tiaramide hydrochloride, tinoridine hydrochloride, epirizole, emorfazone, etc.

Examples of the 5-lipoxygenase inhibitor include Zileuton, docebenone, piripost, SCH-40120, WY-50295, E-6700, ML-3000, TMK-688, ZD-2138, darbufelone mesylate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175, ETH-615, AM-103, MK-0633, etc.

Examples of the 5-lipoxygenase activating protein antagonist include MK-591, MK-886, MK-0633, AM-103, etc.

Examples of the leukotriene synthase inhibitor include auranofin, proglumetacin maleate, L-674636, A-81834, UPA-780, A-93178, MK-886, REV-5901A, SCH-40120, MK-591, Bay-x-1005, Bay-y-1015, DTI-0026, amlexanox, E-6700, etc.

Examples of the prostaglandins (hereinafter referred to briefly as "PG") include PG receptor agonists, PG receptor antagonists, etc.

Examples of the PG receptor include PGE receptors (EP1, EP2, EP3, EP4), PGD receptors (DP, CRTH2), PGF receptor (FP), PGI receptor (IP), TX receptor (TP), etc.

Examples of the antitussive agent include codeine phosphate, dihydrocodeine phosphate, oxymetebanol, dextromethorphan hydrobromide, pentoxyverine citrate, dimemorfan phosphate, oxeladin citrate, chloperastine, benproperine phosphate, clofedanol hydrochloride, fominoben hydrochloride, noscapine, tipepidine hibenzate, eprazinone hydrochloride, plantago herb extract, etc.

Examples of the expectorant agent include foeniculated ammonia spirit, sodium hydrogen carbonate, potassium iodide, bromhexine hydrochloride, cherry bark extract, carbocysteine, fudosteine, ambroxol hydrochloride, controlled release preparation of ambroxol hydrochloride, methylcysteine hydrochloride, acetylcysteine, L-ethylcysteine hydrochloride, tyloxapol, etc.

The above-mentioned other agents are preferably leukotriene receptor antagonists, steroidal agents or sympathomimetic agents.

The dosage form, which is aimed at conducting the present invention into practice, may be in the form of either a pharmaceutical preparation containing the cysLT$_1$/cysLT$_2$ receptor antagonist compound and other medicaments for supplementation and/or enhancement of the treatment effects of the compound formulated in one dosage form, or a pharmaceutical preparation containing each of the ingredients processed individually into separate dosage forms. Such processing into the dosage forms may be carried out in accordance with the known method.

For the above-mentioned purposes, a pharmaceutical composition containing the crystalline form of the present invention or a combination drug of the crystalline form of the present invention with other agents is administered typically systemically or topically, orally or parenterally.

The dosage may vary depending on age, body weight, symptom, treatment effect, administration route, duration of the treatment and the like. Generally, for an adult, from 1 mg to 1,000 mg per dose is orally administered once to several times a day (preferably, once a day), or from 0.1 mg to 100 mg per dose is parenterally (preferably, intravenously) administered once to several times a day, or continuously administered into a vein from 1 to 24 hours a day.

As the dosage may fluctuate according to various conditions as described above, a dose lower than the above-specified dose may in some instances be adequate, whereas a dose in excess of the dose range may in some cases be required.

The compound is administered in the form of solid formulations for oral administration or liquid formulations for oral administration, or injectable formulations, external medicines, suppositories, eye drops, inhalants and the like for parenteral administration, for the purpose of the present invention.

The solid formulations for oral administration include, for example, tablets, pills, capsules, powders, and granules. Capsules include hard capsules and soft capsules.

In such solid formulations for oral administration, one or more active agent(s) are directly formulated according to usual methods, or mixed with one or more of an excipient (lactose, mannitol, glucose, microcrystalline cellulose, starch, etc.), a binding agent (hydroxypropyl cellulose, polyvinylpyrrolidone, magnesium aluminometasilicate, etc.), a disintegrating agent (calcium cellulose glycolate, etc.), a lubricant (magnesium stearate, etc.), a stabilizing agent or a solubilizing agent (glutamic acid, aspartic acid, etc.), and the like. If necessary, the formulations may be coated with a coating agent (such as sugar, gelatin, hydroxypropyl cellulose, or hydroxypropylmethyl cellulose phthalate), or may be coated with two or more layers. Included are also capsules made of absorbable materials such as gelatin.

The liquid formulations for oral administration include pharmaceutically acceptable aqueous solutions, suspensions, emulsions, syrups, elixirs, etc. In such liquid formulations, one or more of the active agent(s) are dissolved, suspended or emulsified in a commonly used diluent (e.g., purified water, ethanol, or a mixture thereof). Furthermore, such liquid formulations may also include wetting agents, suspending agents, emulsifying agents, sweetening agents, flavoring agents, aromatic agents, preservatives, or buffering agents.

The injectable formulations for parenteral administration include, for example, solutions, suspensions, emulsions, and solid formulations for injection which are dissolved, suspended or emulsified into solvent(s) for injection before use. The injectable formulation is prepared by dissolving, suspending or emulsifying one or more active substances in a solvent. Examples of the solvent may include distilled water for injection, saline, vegetable oil, propylene glycol, polyethylene glycol or alcohols such as ethanol, and any combination thereof. The injectable formulation may further contain a stabilizing agent, a solubilizing agent (glutamic acid, aspartic acid, polysorbate 80 (registered trademark), etc.), a suspending agent, an emulsifying agent, a soothing agent, a buffer or a preservative, etc. These are prepared by sterilizing in the final process or by a sterile operation method. Alternatively, they may be used by firstly producing sterile solid formulations such as freeze-dried formulations and dissolving them in sterilized or sterile distilled water for injection or another sterile solvent prior to their use.

The eye drops for parenteral administration may be in the form of liquid eye drops, suspension-type eye drops, emulsion-type eye drops or eye drops which are dissolved in a solvent upon actual use, or eye ointments.

These eye drops are prepared by known methods. For example, in the case of liquid eye drops, they may be prepared by appropriately selecting and incorporating a tonicity agent (sodium chloride, concentrated glycerin, etc.), a buffer (sodium phosphate, sodium acetate, etc.), a surface active agent (Polysorbate 80 (trade name), polyoxyl 40 stearate, polyoxyethylene-hardened castor oil, etc.), a stabilizing agent (sodium citrate, sodium edetate, etc.), and an antiseptic (benzalkonium chloride, Paraben, etc.), and the like, depending on the needs. These are prepared by sterilizing in the final process or by a sterile operation method.

The inhalable formulation for parenteral administration may be in the form of an aerosol, inhalable liquid formulation or inhalable powder. The inhalable liquid formulation may be dissolved, suspended or emulsified in water or other appropriate medium prior to application.

These inhalable formulations may be prepared according to known methods. For example, inhalable liquid formulations may be prepared by appropriately selecting an antiseptic (benzalkonium chloride, Paraben, etc.), a coloring agent, a buffer (sodium phosphate, sodium acetate, etc.), a tonicity agent (sodium chloride, concentrated glycerin, etc.), a thickening agent (carboxyvinyl polymer, etc.), an absorption promoter, and the like, depending on the needs.

Inhalable powders may be prepared by appropriately selecting and incorporating a lubricant (stearic acid, a salt thereof (e.g. magnesium stearate), etc.)), a binding agent (starch, dextrin, etc.), an excipient (lactose, cellulose, etc.), a coloring agent, an antiseptic agent (benzalkonium chloride, Paraben, etc.), an absorption promoter, and the like, depending on the needs.

Inhalable liquid formulations may typically be administered by sprayers (e.g. atomizer, nebulizer, etc.) and inhalable powders may be administered by using inhalers for powder formulations.

Other formulations for parenteral administration include liquid preparations for external application, ointments, liniments, spray formulations, suppositories, pessaries for intravaginal administration, and the like, which contain one or more active substances and may be processed by conventional methods.

The spray formulation includes, besides commonly used diluents, a stabilizing agent such as sodium hydrogen sulfite, and a tonicity-imparting buffer, e.g. a tonicity agent such as sodium chloride, sodium citrate, or citric acid. For the preparation of the spray formulation, details thereof can be found, for example, in U.S. Pat. Nos. 2,868,691 and 3,095,355.

EXAMPLE

Although the present invention will be described in more detail by the following Examples, Biological Examples, Thermodynamical Test, and Photostability test, and it is not limited thereto.

The parenthesized solvents as indicated in the position of chromatographic separation and TLC denote the elution solvents or developing solvents as used, with the ratio being on a volume basis. The parenthesized solvent as indicated under the heading of NMR denotes the solvent used in the measurement.

Compounds in the following Examples were named using ACD/Name (version 6.00, manufactured by Advanced Chemistry Development Inc.).

Example 1

Ethyl 4-(7-bromo-2-methyl-1H-indol-3-yl)butanoate

To a solution of (2-bromophenyl)hydrazine hydrochloride (14 g) in ethanol (60 mL), 5-acetylvaleric acid (9.0 g) was added. The reaction mixture was stirred at 50° C. for 40 minutes, and concentrated sulfuric acid (6.0 mL) was added thereto, followed by heating under reflux for 16 hours. The reaction mixture was added to a saturated aqueous sodium hydrogen carbonate solution which was then extracted with ethyl acetate and dried over anhydrous sodium sulfate, followed by concentration under reduced pressure. The resulting residue was purified by column chromatography (hexane:ethyl acetate=8:1) to obtain the title compound (15 g) having the following physical properties.

TLC:Rf 0.54 (hexane:ethyl acetate=3:1)

$^1$H-NMR (CDCl$_3$): δ 1.23, 1.89-2.00, 2.31, 2.39, 2.72, 4.10, 6.95, 7.24, 7.43, 7.91.

Example 2

Diethyl 4,4'-(7-bromo-2-methyl-1H-indole-1,3-diyl)dibutanoate

The compound (18 g) prepared in Example 1 was dissolved in dimethylsulfoxide (110 mL), and ethyl 4-bromobutyrate (76 g) and cesium carbonate (145 g) were added thereto. The reaction mixture was stirred at 50° C. for 16 hours. Water was added to the reaction mixture, followed by ethyl acetate extraction. The organic layer was dried over magnesium sulfate, and concentrated under reduced pressure. The resulting residue was purified by a medium-pressure preparative liquid chromatograph W-prep 2XY (manufactured by Yamazen Corporation, column: main column 4 L, inject column 3 L; hexane:ethyl acetate=9:1→4:1) to obtain the title compound (24 g) having the following physical properties.

TLC:Rf 0.31 (hexane:acetone=17:3)

$^1$H-NMR (CDCl$_3$): δ 1.24, 1.26, 1.83-1.98, 1.98-2.12, 2.30, 2.36, 2.39, 2.73, 4.09-4.20, 4.47-4.52, 6.88, 7.26, 7.42.

Example 3

Diethyl 4,4'-(7-{[4-(acetyloxy)phenyl]ethynyl}-2-methyl-1H-indole-1,3-diyl)dibutanoate To a solution of the compound (5.5 g) prepared in Example 2 and 4-ethynylphenyl acetate (3.8 g) in acetonitrile (25 mL), diisopropylamine (3.3 mL) and bis(tri-tert-butylphosphine)palladium (320 mg) were added under an argon atmosphere, followed by stirring at room temperature for 15 hours. The reaction mixture was filtered through Celite®, and the filtrate was concentrated. The resulting residue was purified by a medium-pressure preparative liquid chromatograph W-prep 2XY (manufactured by Yamazen Corporation, column: main column 3L, inject column 2L; hexane:ethyl acetate=9:1→7:3) to obtain the title compound (5.9 g) having the following physical properties.

TLC:Rf 0.26 (hexane:ethyl acetate=3:1)

$^1$H-NMR (CDCl$_3$): δ 1.21, 1.24, 1.86-1.98, 2.10-2.22, 2.25-2.37, 2.75, 4.04-4.14, 4.59-4.65, 7.03, 7.11, 7.32, 7.50, 7.55.

Example 4

Diethyl 4,4'-{7-[(4-hydroxyphenyl)ethynyl]-2-methyl-1H-indole-1,3-diyl}dibutanoate Potassium carbonate (3.1 g) was added to a solution of the compound (5.9 g) prepared in Example 3 in ethanol (11 mL) and dimethoxyethane (11 mL), followed by stirring at room temperature for 15 hours. The reaction mixture was diluted with water, and extracted with ethyl acetate. The organic layer was washed sequentially with water and brine, dried over magnesium sulfate, followed by concentration under reduced pressure. The resulting residue was purified by a medium-pressure preparative liquid chromatograph W-prep 2XY (manufactured by Yamazen Corporation, column: main column 2L, inject column L; hexane:ethyl acetate=9:1→6:4) to obtain the title compound (4.8 g) having the following physical properties.

TLC:Rf 0.29 (hexane:ethyl acetate=2:1)
$^1$H-NMR (CDCl$_3$): δ 1.22, 1.26, 1.82-1.99, 2.05-2.21, 2.32, 2.36, 2.75, 4.04-4.14, 4.62, 5.39, 6.83, 7.01, 7.30, 7.42, 7.48.

Example 5

4-(pentafluorophenyl)but-3-yn-1-ol

To a solution of 1-bromo-2,3,4,5,6-pentafluorobenzene (50 g) in triethylamine (200 mL), 3-butyn-1-ol (15 g), triphenylphosphine (2.7 g), dichlorobistriphenylphosphinepalladium (3.6 g) and copper (I) iodide (1.9 g) were added, followed by stirring at 80° C. for 16 hours. The reaction mixture was cooled to room temperature, and tert-butyl methyl ether (500 mL) was added thereto, followed by stirring at 0° C. for 30 minutes. The reaction mixture was filtered through Celite®, and the filtrate was concentrated. The resulting residue was purified by flash column chromatography (hexane:ethyl acetate=95:5→65:35) to give the title compound (43 g) having the following physical properties.

TLC:Rf 0.28 (hexane:ethyl acetate=4:1)
$^1$H-NMR (CDCl$_3$): δ 1.81, 2.78, 3.86.

Example 6

4-(pentafluorophenyl)butan-1-ol

To a solution of the compound (43 g) prepared in Example 5 in ethanol (430 mL), 10% palladium carbon (50% water content, 4.3 g) was added. The atmosphere inside the reaction system was replaced with argon, followed by stirring at room temperature under a hydrogen atmosphere for 6 hours. Thereto, 10% palladium carbon (50% water content, 4.3 g) was added, followed by stirring at room temperature under a hydrogen atmosphere for 2 hours. The reaction mixture was filtered through Celite®, and the filtrate was concentrated to obtain the title compound (41 g) having the following physical properties.

TLC:Rf 0.31 (hexane:ethyl acetate=4:1)
$^1$H-NMR (CDCl$_3$): δ 1.20-1.38, 1.52-1.76, 2.74, 3.68.

Example 7

4-(pentafluorophenyl)butyl 4-methylbenzene sulfonate

Triethylamine (46 mL) was added to a solution of the compound (40 g) prepared in Example 6 in toluene (330 mL), followed by stirring at 0° C. p-toluenesulfonyl chloride (41 g) and trimethylamine hydrochloride (1.6 g) were added thereto, followed by stirring at 0° C. for 2 hours, and at room temperature for another 20 hours. The reaction mixture was cooled to 0° C., and N,N-dimethylethane-1,2-diamine (7.3 g) was added thereto, followed by stirring for 15 minutes. Water was added to the reaction mixture, and the aqueous layer was made acidic by addition of 2N hydrochloric acid, followed by separation of the organic layer. The aqueous layer was extracted with toluene; the combined organic layer was washed sequentially with water and saturated brine; and dried over anhydrous magnesium sulfate and filtered, followed by evaporation of the solvent under reduced pressure. The solid components were washed with hexane-ethyl acetate (10:1) to obtain the title compound (52 g) having the following physical properties.

TLC:Rf 0.48 (hexane:ethyl acetate=5:1)
$^1$H-NMR (CDCl$_3$): δ 1.55-1.77, 2.45, 2.66, 4.05, 7.35, 7.78.

Example 8

Diethyl 4,4'-[2-methyl-7-({4-[4-(pentafluorophenyl) butoxy]phenyl}ethynyl)-1H-indole-1,3-diyl]dibutanoate Cesium carbonate (220 mg) was added to solution of the compound (180 mg) prepared in Example 4 and the compound (150 mg) prepared in Example 7 in N,N-dimethylformamide (1.0 mL), followed by stirring at room temperature for 10 hours. The reaction mixture was diluted with water, and extracted with ethyl acetate. The organic layer was washed sequentially with water and saturated brine and dried over magnesium sulfate, followed by concentration under reduced pressure. The resulting residue was purified by a medium-pressure preparative liquid chromatograph W-prep 2XY (manufactured by Yamazen Corporation, column: main column M, inject column S; hexane:ethyl acetate=9:1→8:2) to obtain the title compound (160 mg) having the following physical properties.

TLC:Rf 0.52 (hexane:ethyl acetate=3:1)
$^1$H-NMR(CDCl$_3$): δ 1.19-1.26, 1.71-2.00, 2.05-2.10, 2.25-2.40, 2.68-2.85, 3.99-4.18, 4.62, 6.87, 7.01, 7.31, 7.42-7.52.

Example 9

4,4'-[2-methyl-7-({4-[4-(pentafluorophenyl)butoxy] phenyl}ethynyl)-1H-indole-1,3-diyl]dibutanoic acid (compound II)

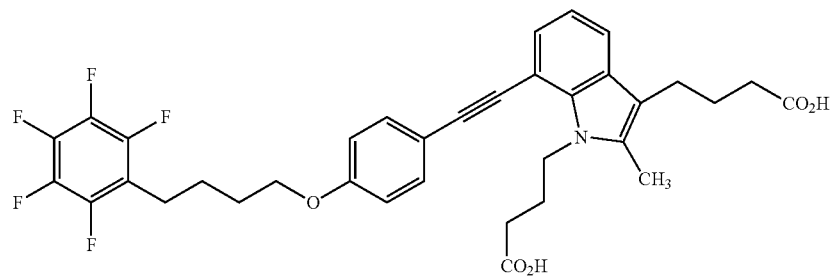 [SMILES: Cc1c(CCCC(=O)O)c2cccc(C#Cc3ccc(OCCCCc4c(F)c(F)c(F)c(F)c4F)cc3)c2n1CCCC(=O)O]

A 2N aqueous sodium hydroxide solution (1.0 mL) was added to a solution of the compound (150 mg) prepared in Example 8 in dimethoxyethane (2.0 mL) and ethanol (2.0 mL), followed by stirring at room temperature for 4 hours. Ice-cold 2N hydrochloric acid (1.0 mL) was added under ice-cooling to the reaction mixture, followed by extraction with ethyl acetate. The organic layer was washed sequentially with water and saturated brine, dried over magnesium sulfate, followed by concentration under reduced pressure. The resulting residue was washed with diisopropylether-hexane (9:1), and dried under reduced pressure to obtain the title compound (120 mg) having the following physical properties.

TLC:Rf 0.40 (methylene chloride:methanol=9:1)
$^1$H-NMR (DMSO-D$_6$): δ 1.63-1.82, 1.87-2.02, 2.14-2.24, 2.33, 2.67, 2.76, 4.03, 4.54, 6.94-7.03, 7.22, 7.44-7.54, 12.08.

Example 10

4,4'-[4-fluoro-2-methyl-7-({4-[4-(pentafluorophenyl)butoxy]phenyl}ethynyl)-1H-indole-1,3-diyl]dibutanoic acid

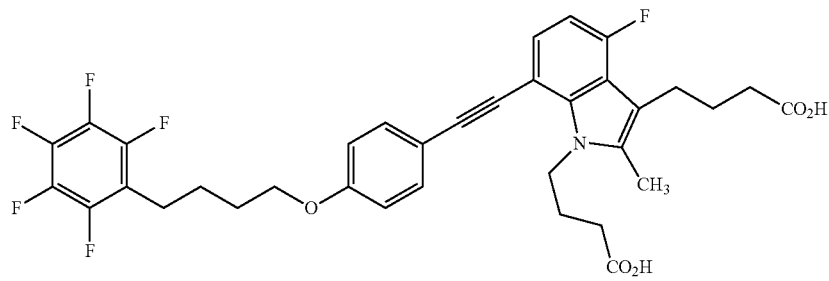 [SMILES: Cc1c(CCCC(=O)O)c2c(F)ccc(C#Cc3ccc(OCCCCc4c(F)c(F)c(F)c(F)c4F)cc3)c2n1CCCC(=O)O]

(2-bromo-5-fluorophenyl)hydrazine was produced according to the following production method: 2-bromo-5-fluoroaniline (20 g) was poured into 5N hydrochloric acid (200 mL) under ice-cooling, followed by stirring for 20 minutes, and a solution of sodium nitrite (8.0 g) in water (20 mL) was slowly added thereto, followed by stirring for 40 minutes. The reaction mixture and a 5N aqueous sodium hydroxide solution (150 mL) were added under ice-cooling to an aqueous solution (200 mL) of sodium sulfite (33 g) and sodium dihydrogen phosphate (1.7 g) with maintaining a pH of 6 or higher, followed by stirring at 75° C. for 1 hour. The reaction mixture was cooled to room temperature and filtered, and the filtrate was concentrated under reduced pressure. The resulting residue was poured into concentrated hydrochloric acid at 60° C., followed by stirring for 2 hours, and at room temperature overnight. The reaction mixture was neutralized under ice-cooling with an aqueous 12N sodium hydroxide solution. The precipitated solid was filtered; washed with water; and dissolved in ethyl acetate. The organic layer was dried over magnesium sulfate, and concentrated under reduced pressure to obtain a hydrazine compound. By the same procedure as in Example 1→Example 2→Example 3→Example 4→Example 8→Example 9 using (2-bromo-5-fluorophenyl) hydrazine instead of (2-bromophenyl)hydrazine hydrochloride, the compound of the present invention having the following physical properties was obtained.

TLC:Rf 0.43 (methylene chloride:methanol=9:1)
$^1$H-NMR (DMSO-D$_6$): δ 1.64-1.84, 1.88-2.02, 2.14-2.23, 2.33, 2.68-2.82, 4.02, 4.49-4.59, 6.76, 6.97, 7.19, 7.47, 12.08.

Examples 10 (1) to (2)

By the same procedure as in Example 1→Example 2→Example 3→Example 4→Example 8→Example 9 using (2-bromo-5-fluorophenyl)hydrazine instead of (2-bromophenyl)hydrazine hydrochloride, and using the corresponding sulfonate instead of the compound prepared in Example 7, the compounds of the present invention having the following physical properties were obtained.

Example 10 (1)

4,4'-[4-fluoro-7-({4-[4-(3-fluoro-2-methylphenyl)butoxy]phenyl}ethynyl)-2-methyl-1H-indole-1,3-diyl]dibutanoic acid (compound I)

TLC:Rf 0.58 (methylene chloride:methanol=9:1);
$^1$H-NMR (DMSO-D$_6$): δ 1.59-1.85, 1.87-2.05, 2.10-2.26, 2.32, 2.59-2.82, 4.05, 4.48-4.63, 6.76, 6.91-7.06, 7.08-7.16, 7.20, 7.48, 12.08.

Example 10 (2)

4,4'-[4-fluoro-2-methyl-7-({4-[4-(2,3,4,6-tetrafluorophenyl)butoxy]phenyl}ethynyl)-1H-indole-1,3-diyl]dibutanoic acid (compound III)

TLC:Rf 0.57 (methylene chloride:methanol=9:1);
$^1$H-NMR (DMSO-D$_6$): δ 1.61-1.83, 1.87-2.02, 2.13-2.23, 2.32, 2.64-2.79, 4.02, 4.49-4.61, 6.76, 6.97, 7.20, 7.38-7.58, 12.08.

Example 11

Type B crystal of 4,4'-[4-fluoro-7-({4-[4-(3-fluoro-2-methylphenyl)butoxy]phenyl}ethynyl)-2-methyl-1H-indole-1,3-diyl]dibutanoic acid (compound I)

The compound (500 mg) prepared in Example 10(1) was resolved in toluene (300 mL) at 80° C. This solution was added to n-heptane (150 mL) dropwise at 50° C. or lower. After cooling to 0° C., The precipitated solid was filtered and dried under reduced pressure to obtain the title compound (490 mg).

The powdered X-ray diffraction spectrum and differential scanning calorimetry (DSC) data of the crystal measured under the following conditions are shown in FIG. 1 and FIG. 2, respectively.
(1) Powdered X-Ray Diffraction Spectrum
Apparatus: BRUKER axs, D8 DISCOVER with GADDS
Target: Cu
Voltage: 40 kV
Current: 40 mA.

The crystal can be characterized by the powdered X-ray diffraction spectrum obtained with Cu—Kα radiation with the diffraction angle (2θ) and relative intensity as shown in Table 1 below.

TABLE 1

| diffraction angle (2θ) | relative intensity |
|---|---|
| 5.34 | 100 |
| 10.99 | 4 |
| 11.58 | 7 |
| 12.49 | 5 |
| 14.25 | 24 |
| 15.76 | 12 |
| 16.43 | 34 |
| 19.03 | 9 |
| 19.56 | 7 |
| 21.03 | 16 |
| 21.54 | 9 |
| 23.16 | 9 |
| 24.18 | 8 |

(2) Differential Scanning Calorimetry (DSC)
Apparatus: METTLER TOLEDO, DSC822e Differential scanning calorimetry apparatus
Amount of Sample: 1.14 mg
Sample Cell Aluminum pan (40 μL)
Flow Rate of $N_2$ Gas: 40 mL/min
Programming Rate: 5° C./min (Scan range: 25-300° C.)

Type B crystal of compound I have a first endothermic peak of about 127° C., a second endothermic peak of about 146° C., and a third endothermic peak of about 157° C. The peak at 127° C. corresponds to the melting of type B crystal. The peaks at 146° C. and 157° C. correspond to the melting of type A crystal and type C crystal, respectively.

Example 12

Type C crystal of 4,4'-[4-fluoro-7-({4-[4-(3-fluoro-2-methylphenyl)butoxy]phenyl}ethynyl)-2-methyl-1H-indole-1,3-diyl]dibutanoic acid (compound I)

To the compound (30 mg) prepared in Example 10(1) was added a mixed solvent of acetone (0.3 mL) and water (0.3 mL). The mixture was heated to 70° C., and stirred at 70° C. for 15 hours. Then, the mixture was cooled to 25° C., and stirred at 25° C. for 3 hours. The precipitated solid was filtered and dried under reduced pressure to obtain the title compound (29 mg).

The powdered X-ray diffraction spectrum and differential scanning calorimetry (DSC) data of the crystal measured under the following conditions are shown in FIG. 3 and FIG. 4, respectively.
(1) Powdered X-Ray Diffraction Spectrum
Apparatus: BRUKER axs, D8 DISCOVER with GADDS
Target: Cu
Voltage: 40 kV
Current: 40 mA.

The crystal can be characterized by the powdered X-ray diffraction spectrum obtained with Cu—Kα radiation with the diffraction angle (2θ) and relative intensity as shown in Table 2 below.

TABLE 2

| diffraction angle (2θ) | relative intensity |
|---|---|
| 6.41 | 6 |
| 7.29 | 18 |
| 9.22 | 6 |
| 10.03 | 14 |
| 10.24 | 24 |
| 12.15 | 24 |
| 12.59 | 15 |
| 13.36 | 62 |
| 13.88 | 11 |
| 14.15 | 13 |
| 14.44 | 11 |
| 16.60 | 14 |
| 17.33 | 10 |
| 17.95 | 24 |
| 18.44 | 26 |
| 18.86 | 19 |
| 19.27 | 10 |
| 20.23 | 21 |
| 21.10 | 100 |
| 21.85 | 27 |
| 22.26 | 18 |
| 23.11 | 15 |
| 23.63 | 13 |
| 24.38 | 43 |

(2) Differential Scanning Calorimetry (DSC)
Apparatus: METTLER TOLEDO, DSC822e Differential scanning calorimetry apparatus
Amount of Sample: 7.67 mg
Sample Cell Aluminum pan (40 μL)
Flow Rate of $N_2$ Gas: 40 mL/min
Programming Rate: 5° C./min (Scan range: 25-300° C.)

Type C crystal of compound I has an endothermic peak at 157° C., which corresponds to the melting of type C crystal.

Example 13

Type C crystal of 4,4'-[4-fluoro-7-({4-[4-(3-fluoro-2-methylphenyl)butoxy]phenyl}ethynyl)-2-methyl-1H-indole-1,3-diyl]dibutanoic acid (compound I)

Type C crystal of 4,4'-[4-fluoro-7-({4-[4-(3-fluoro-2-methylphenyl)butoxy]phenyl}ethynyl)-2-methyl-1H-indole-1,3-diyl]dibutanoic acid as shown in Example 12 can be also produced by the following method.

To the compound (10 mg) prepared in Example 10(1) was added a mixed solvent of acetone (80 mL) and water (8 mL) at room temperature. Water (30 mL) was added, and 10 mg of seed crystal was added. Then water (12 mL) was added, stirred at 55° C. for 2 hours and a half, and subsequently cooled to room temperature. After stirring at room temperature for 30 minutes, the precipitated solid was filtered and dried under reduced pressure to obtain the title compound (9.68 g).

Example 14

Type B crystal of 4,4'-[2-methyl-7-({4-[4-(pentafluorophenyl)butoxy]phenyl}ethynyl)-1H-indole-1,3-diyl]dibutanoic acid (compound II)

The compound (93.8 g) prepared in Example 9 was resolved in a mixed solvent of ethanol (1.23 L) and water (308 mL) at 72° C. The hot mixture was filtered, washed with a mixed solvent of ethanol (27 mL) and water (68 mL), and allowed to cool. After cooling its inner temperature to 22° C., the precipitated solid was filtered and dried under reduced pressure to obtain the title compound (91.2 g).

The powdered X-ray diffraction spectrum and differential scanning calorimetry (DSC) data of the crystal measured under the following conditions are shown in FIG. 5 and FIG. 6, respectively.

(1) Powdered X-Ray Diffraction Spectrum
Apparatus: BRUKER axs, D8 DISCOVER with GADDS
Target: Cu
Voltage: 40 kV
Current: 40 mA.

The crystal can be characterized by the powdered X-ray diffraction spectrum obtained with Cu—Kα radiation with the diffraction angle (2θ) and relative intensity as shown in Table 3 below.

TABLE 3

| diffraction angle (2θ) | relative intensity |
| --- | --- |
| 5.12 | 100 |
| 8.94 | 6 |
| 9.22 | 9 |
| 10.16 | 9 |
| 10.51 | 15 |
| 12.07 | 25 |
| 13.07 | 82 |
| 13.62 | 19 |
| 14.37 | 13 |
| 14.90 | 49 |
| 15.35 | 10 |
| 16.05 | 12 |
| 16.92 | 56 |
| 17.52 | 7 |
| 17.86 | 8 |
| 18.61 | 10 |
| 19.58 | 10 |
| 19.92 | 31 |
| 20.42 | 38 |
| 21.19 | 40 |
| 21.71 | 20 |
| 22.03 | 27 |
| 22.39 | 18 |
| 23.74 | 10 |
| 24.24 | 76 |

(2) Differential Scanning Calorimetry (DSC)
Apparatus: METTLER TOLEDO, DSC822e Differential scanning calorimetry apparatus
Amount of Sample: 3.27 mg
Sample Cell: Aluminum pan (40 μL)
Flow Rate of $N_2$ Gas: 40 mL/min
Programming Rate: 5° C./min (Scan range: 25-300° C.)

Type B crystal of compound II has a endothermic peak at 146° C., which corresponds to the melting of type B crystal.

Example 15

Type B crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid (compound III)

The compound (50 mg) prepared in Example 10(2) was dissolved in a mixed solvent of 2-propanol (0.8 mL) and water (0.2 mL) at 80° C. After cooling to 0° C., the precipitated solid was filtered and dried under reduced pressure to obtain the title crystal (24 mg).

Figure 7:
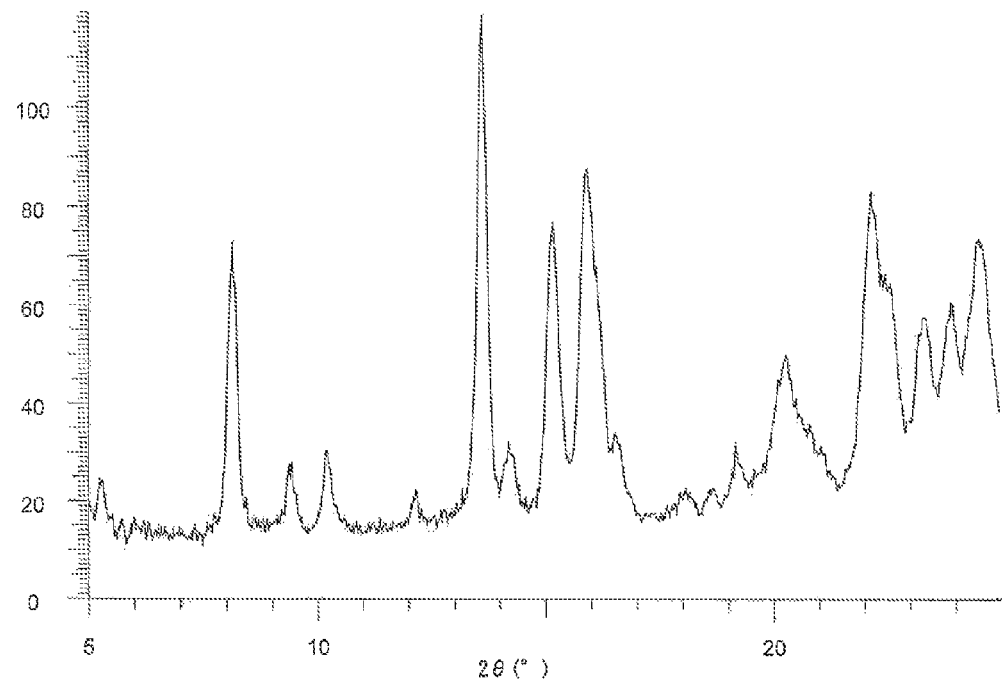
FIG. 7 shows a chart of powdered X-ray diffraction spectrum of type B crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid.
Figure 8:
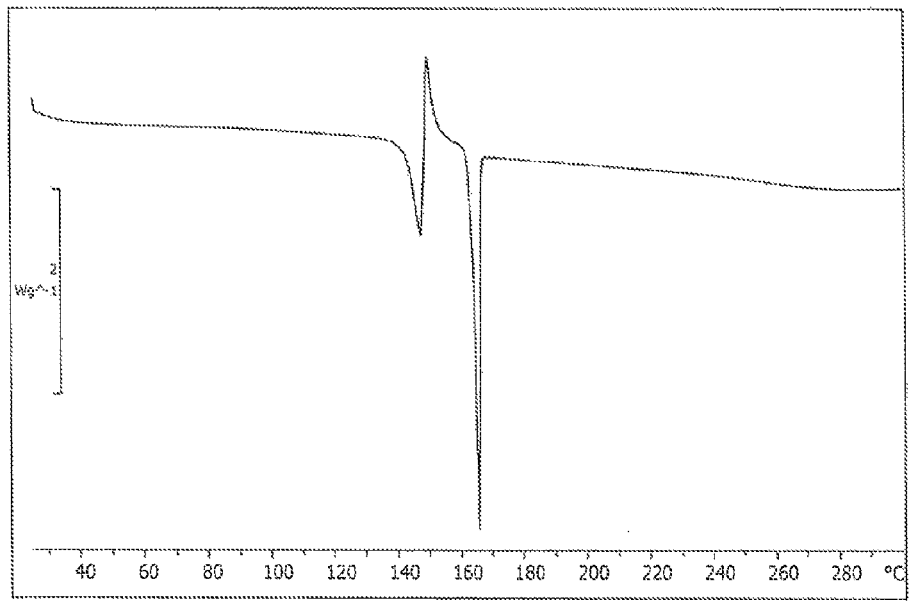
FIG. 8 shows a chart of differential scanning calorimetry (DSC) of type B crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid.

The powdered X-ray diffraction spectrum and differential scanning calorimetry (DSC) data of the crystal measured under the following conditions are shown in FIG. 7 and FIG. 8, respectively.
(1) Powdered X-Ray Diffraction Spectrum
Apparatus: BRUKER axs, D8 DISCOVER with GADDS
Target: Cu
Voltage: 40 kV
Current: 40 mA.

The crystal can be characterized by the powdered X-ray diffraction spectrum obtained with Cu—Kα radiation with the diffraction angle (2θ) and relative intensity as shown in Table 4 below.

TABLE 4

| diffraction angle (2θ) | relative intensity |
| --- | --- |
| 5.26 | 20 |
| 5.99 | 14 |
| 8.12 | 61 |
| 9.37 | 23 |
| 10.20 | 26 |
| 12.13 | 19 |
| 13.61 | 100 |
| 14.23 | 27 |
| 15.17 | 65 |
| 15.92 | 74 |
| 16.55 | 29 |
| 18.03 | 19 |
| 18.65 | 19 |
| 19.20 | 25 |
| 20.28 | 42 |
| 22.18 | 70 |
| 22.50 | 56 |
| 23.35 | 48 |
| 23.92 | 51 |
| 24.55 | 62 |

(2) Differential Scanning Calorimetry (DSC)
Apparatus: METTLER TOLEDO, DSC822e Differential scanning calorimetry apparatus
Amount of Sample: 1.10 mg
Sample Cell Aluminum pan (40 μL)
Flow Rate of $N_2$ Gas: 40 mL/min
Programming Rate: 5° C./min (Scan range: 25-300° C.)

Type B crystal of the compound III have a first endothermic peak of about 144° C., a second endothermic peak of about 164° C. The peak at 144° C. corresponds to the melting of type B crystal. The peak at 164° C. corresponds to the melting of type A crystal.

Example 16

Type C crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid (compound III)

The compound (500 mg) prepared in Example 10(2) was dissolved in ethanol (15 mL) at 65° C., and this solution was added to water (7.5 mL) dropwise at inner temperature of 25° C. or lower. The precipitated solid was filtered and dried under reduced pressure to obtain the title compound (475 mg).

Figure 9:
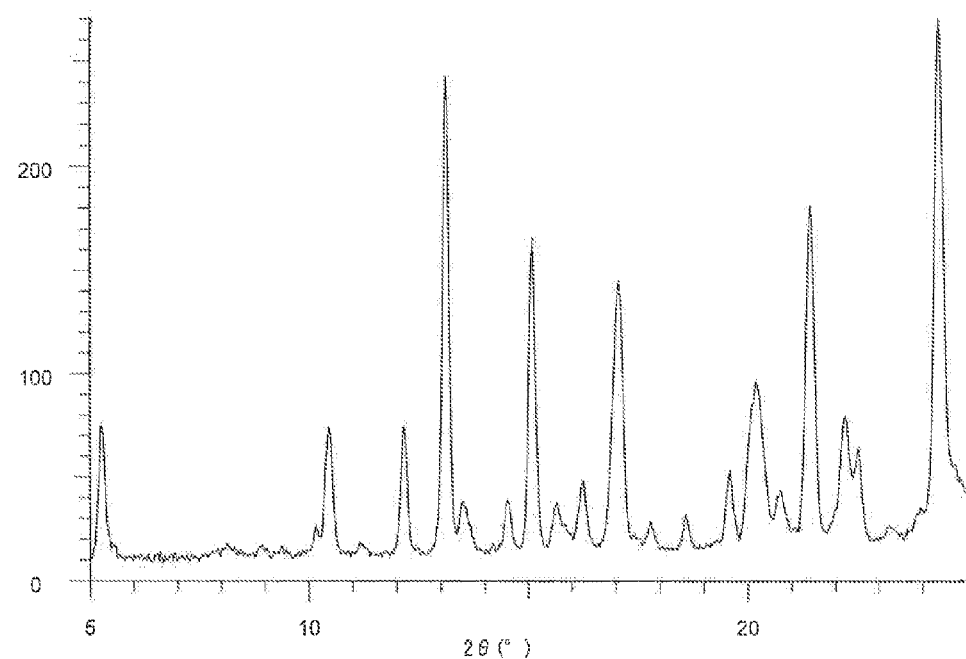
FIG. 9 shows a chart of powdered X-ray diffraction spectrum of type C crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid.
Figure 10:
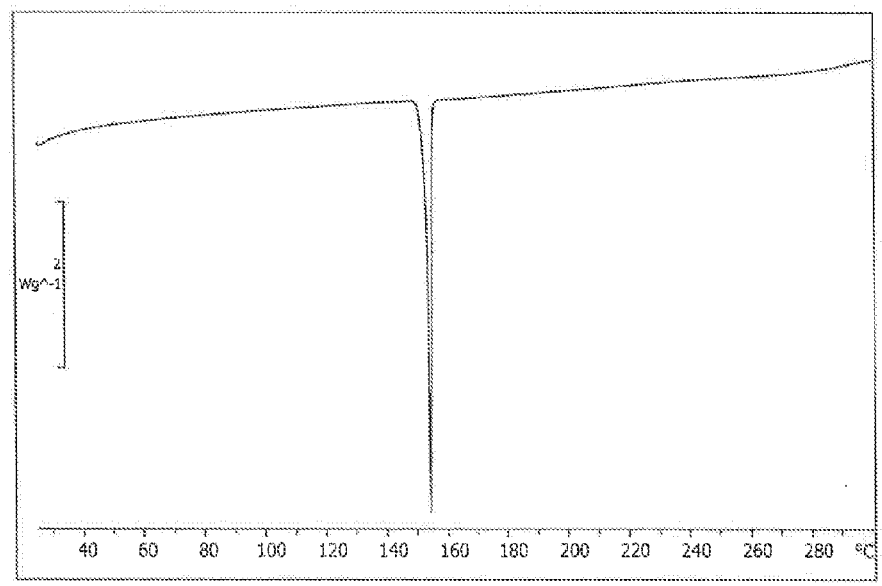
FIG. 10 shows a chart of differential scanning calorimetry (DSC) of type C crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid.

The powdered X-ray diffraction spectrum and differential scanning calorimetry (DSC) data of the crystal measured under the following conditions are shown in FIG. 9 and FIG. 10, respectively.
(1) Powdered X-Ray Diffraction Spectrum
Apparatus: BRUKER axs, D8 DISCOVER with GADDS
Target: Cu
Voltage: 40 kV
Current: 40 mA.

The crystal can be characterized by the powdered X-ray diffraction spectrum obtained with Cu—Kα radiation with the diffraction angle (2θ) and relative intensity as shown in Table 5 below.

TABLE 5

| diffraction angle (2θ) | relative intensity |
| --- | --- |
| 5.25 | 28 |
| 8.12 | 7 |
| 8.92 | 6 |

TABLE 5-continued

| diffraction angle (2θ) | relative intensity |
| --- | --- |
| 10.45 | 27 |
| 11.19 | 7 |
| 12.16 | 28 |
| 13.12 | 90 |
| 13.51 | 14 |
| 14.54 | 14 |
| 15.08 | 61 |
| 15.65 | 14 |
| 16.25 | 18 |
| 17.07 | 54 |
| 17.80 | 11 |
| 18.61 | 12 |
| 19.59 | 20 |
| 20.21 | 36 |
| 20.75 | 16 |
| 21.44 | 67 |
| 22.23 | 29 |
| 22.53 | 24 |
| 23.29 | 10 |
| 24.41 | 100 |

(2) Differential Scanning Calorimetry (DSC)
Apparatus: METTLER TOLEDO, DSC822e Differential scanning calorimetry apparatus
Amount of Sample: 3.28 mg
Sample Cell Aluminum pan (40 μL)
Flow Rate of $N_2$ Gas: 40 mL/min
Programming Rate: 5° C./min (Scan range: 25-300° C.)
Type C crystal of compound III has a endothermic peak at 152° C., which corresponds to the melting of type C crystal.

Comparative Example 1

Type A crystal of 4,4'-[4-fluoro-7-({4-[4-(3-fluoro-2-methylphenyl)butoxy]phenyl}ethynyl)-2-methyl-1H-indole-1,3-diyl]dibutanoic acid (compound I)

Figure 11:
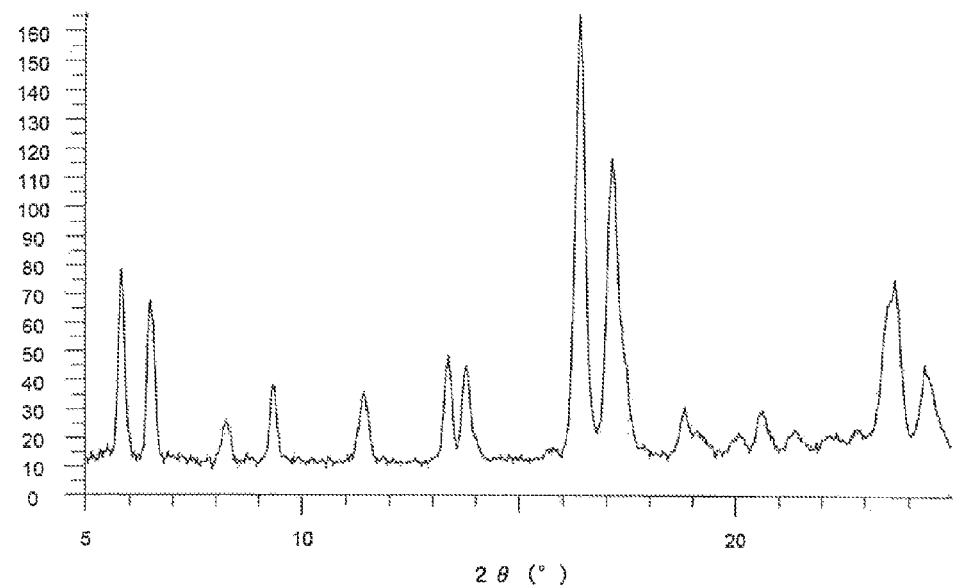
FIG. 11 shows a chart of powdered X-ray diffraction spectrum of type A crystal of 4,4'-[4-fluoro-7-({4-[4-(3-fluoro-2-methylphenyl)butoxy]phenyl}ethynyl)-2-methyl-1H-indole-1,3-diyl]dibutanoic acid.
Figure 12:
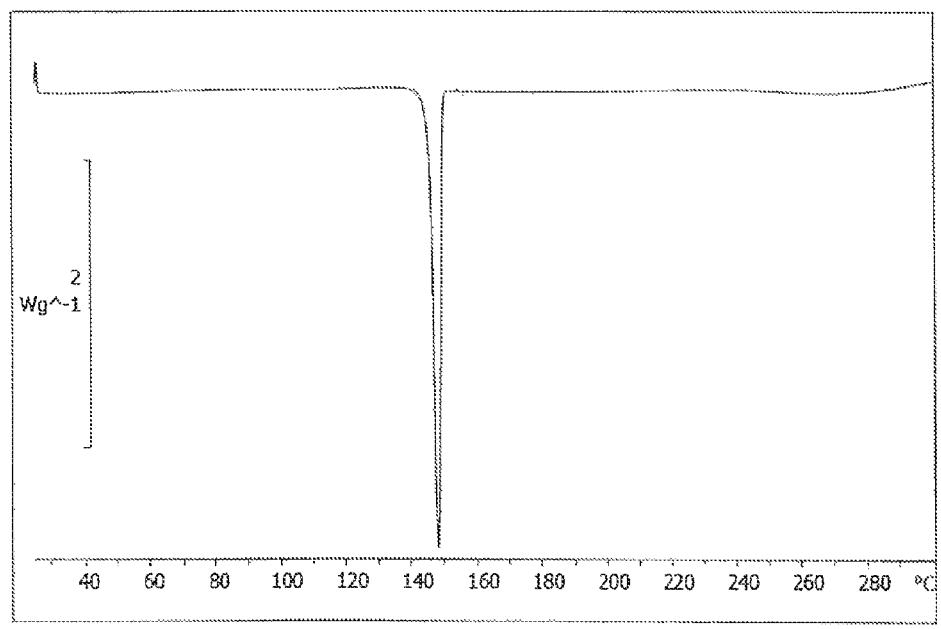
FIG. 12 shows a chart of differential scanning calorimetry (DSC) of type A crystal of 4,4'-[4-fluoro-7-({4-[4-(3-fluoro-2-methylphenyl)butoxy]phenyl}ethynyl)-2-methyl-1H-indole-1,3-diyl]dibutanoic acid.

The compound (30 mg) prepared in Example 10(1) was dissolved in methyl tertiary butyl ether (2.4 mL) at 60° C. The solution was cooled to room temperature. The crystal was filtered and dried under reduced pressure to obtain the title compound (24 mg).
The powdered X-ray diffraction spectrum and differential scanning calorimetry (DSC) data of the crystal measured under the following conditions are shown in FIG. 11 and FIG. 12, respectively.
(1) Powdered X-Ray Diffraction Spectrum
Apparatus: BRUKER axs, D8 DISCOVER with GADDS
Target: Cu
Voltage: 40 kV
Current: 40 mA.
(2) Differential Scanning Calorimetry (DSC)
Apparatus: METTLER TOLEDO, DSC822e Differential scanning calorimetry apparatus
Amount of Sample: 3.30 mg
Sample Cell Aluminum pan (40 μL)
Flow Rate of N2 Gas: 40 mL/min
Programming Rate: 5° C./min (Scan range: 25-300° C.)
Type A crystal of compound I has an endothermic peak at 146° C., which corresponds to the melting of type A crystal.

Comparative Example 2

Type A crystal of 4,4'-[2-methyl-7-({4-[4-(pentafluorophenyl)butoxy]phenyl}ethynyl)-1H-indole-1,3-diyl]dibutanoic acid (compound II)

Figure 13:
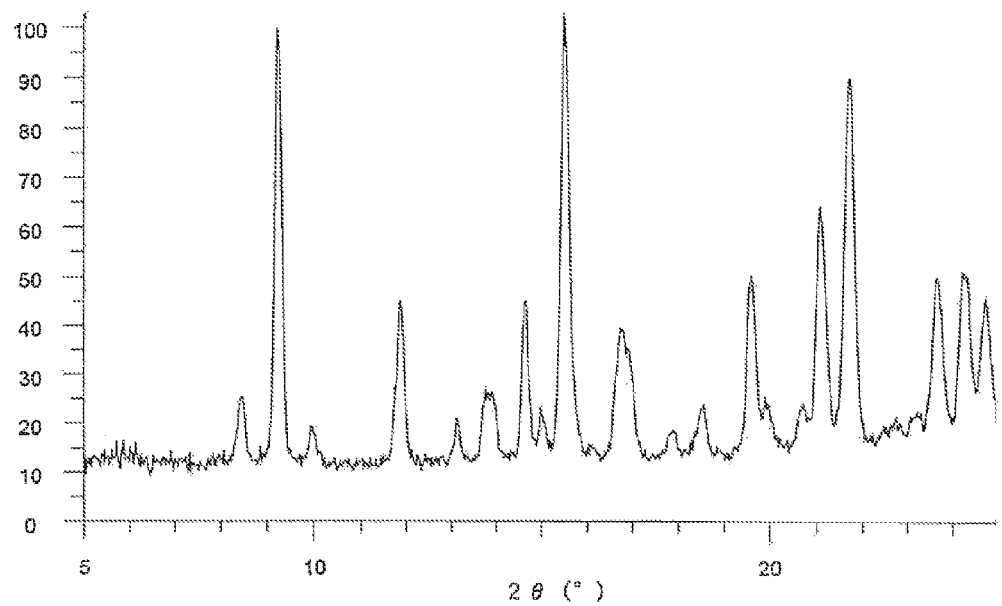
FIG. 13 shows a chart of powdered X-ray diffraction spectrum of type A crystal of 4,4'-[2-methyl-7-({4-[4-(pentafluorophenyl)butoxy]phenyl}ethynyl)-1H-indole-1,3-diyl]dibutanoic acid.
Figure 14:
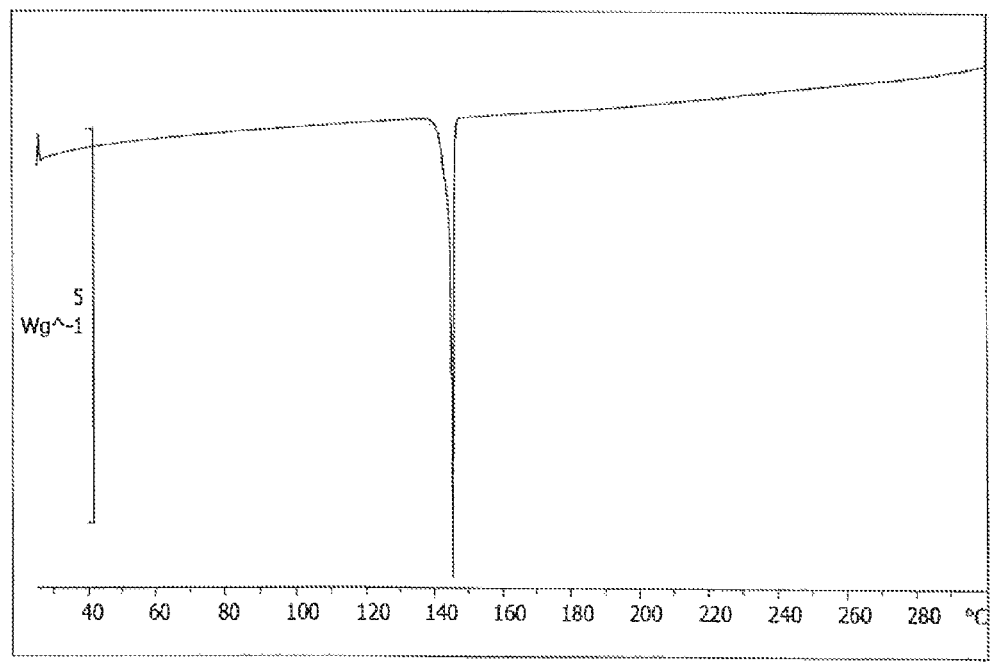
FIG. 14 shows a chart of differential scanning calorimetry (DSC) of type A crystal of 4,4'-[2-methyl-7-({4-[4-(pentafluorophenyl)butoxy]phenyl}ethynyl)-1H-indole-1,3-diyl]dibutanoic acid.

The compound (50 mg) prepared in Example 9 was dissolved in methyl tertiary butyl ether (1.5 mL) at 50° C. To the solution, n-heptane (0.75 mL) was added at room temperature, which was then allowed to stand for 30 minutes. The crystal was filtered and dried under reduced pressure to obtain the title compound (39 mg).
The powdered X-ray diffraction spectrum and differential scanning calorimetry (DSC) data of the crystal measured under the following conditions are shown in FIG. 13 and FIG. 14, respectively.
(1) Powdered X-Ray Diffraction Spectrum
Apparatus: BRUKER axs, D8 DISCOVER with GADDS
Target: Cu
Voltage: 40 kV
Current: 40 mA.
(2) Differential Scanning Calorimetry (DSC)
Apparatus: METTLER TOLEDO, DSC822e Differential scanning calorimetry apparatus
Amount of Sample: 1.37 mg
Sample Cell Aluminum pan (40 μL)
Flow Rate of $N_2$ Gas: 40 mL/min
Programming Rate: 5° C./min (Scan range: 25-300° C.)
Type A crystal of compound II has an endothermic peak at 143° C., which corresponds to the melting of type A crystal.

Comparative Example 3

Type A crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid (compound III)

The compound (50 mg) prepared in Example 10 (2) was dissolved in ethyl acetate (1.4 mL) at 70° C. To the solution, n-heptane (0.68 mL) was added at room temperature, which was then cooled to 0° C. The crystal was filtered and dried under reduced pressure to obtain the title compound (39 mg).
The powdered X-ray diffraction spectrum and differential scanning calorimetry (DSC) data of the crystal measured under the following conditions are shown in FIG. 15 and FIG. 16, respectively.
(1) Powdered X-Ray Diffraction Spectrum
Apparatus: BRUKER axs, D8 DISCOVER with GADDS
Target: Cu
Voltage: 40 kV
Current: 40 mA.
(2) Differential Scanning Calorimetry (DSC)
Apparatus: METTLER TOLEDO, DSC822e Differential scanning calorimetry apparatus
Amount of Sample: 4.70 mg
Sample Cell: Aluminum pan (40 μL)
Flow Rate of $N_2$ Gas: 40 mL/min
Programming Rate: 5° C./min (Scan range: 25-300° C.)
Type A crystal of compound III has an endothermic peak at 164° C., which corresponds to the melting of type A crystal.
The effects of the crystalline form of the present invention can be verified according to the following experiments. Although the experimental methods are described below, the present invention is not limited thereto.

Biological Example 1

Effects of Compounds on $LTD_4$-Induced Increase in Intracellular Calcium Levels Chinese hamster ovary (CHO) cells expressing the human $cysLT_1$ receptor were seeded at a density of $0.4 \times 10^5$ cells/well into a 96-well plate and cultured in an F-12 medium at 37° C. in the presence of 5% $CO_2$ for 24 hours. The cells were incubated in the culture medium containing 7.5 μM Fura2-

AM, 20 mM 2-[4-(2-hydroxyethyl)-1-piperazinyl]ethanesulfonic acid (HEPES) and 2.5 mM probenecid, at 37° C. for about 60 minutes. The Fura2-AM-loaded cells were washed once with assay buffer (Hank's buffer containing 20 mM HEPES), and the $LTD_4$-induced intracellular calcium influx was measured using a FDSS2000 (manufactured by Hamamatsu Photonics K.K.). The crystalline forms of the present invention were treated 30 minutes prior to $LTD_4$ stimulation, and time-course changes of the response provoked by 100 nM of $LTD_4$ was measured over 150 seconds. The receptor antagonistic activity of the crystalline form of the present invention were evaluated in terms of a maximum fluorescence intensity obtained up to 150 seconds after $LTD_4$ stimulation, and a 50% inhibitory concentration (($IC_{50}$) was calculated for each compound.

As a result, type C crystal of compound I (the compound was prepared in Example 12), type B crystal of compound II (the compound was prepared in Example 14), and type C crystal of compound III (the compound was prepared in Example 16) showed $IC_{50}$ values of 1.8, 1.1, and 7.0 nM, respectively.

Biological Example 2

Effects of Compounds on $LTD_4$-Induced Increase in Intracellular Calcium Levels HEK293 cells expressing the human $cysLT_2$ receptor were seeded at a density of $1 \times 10^5$ cells/well into a 96-well plate and cultured in a Dulbecco's Modified Eagle Medium (DMEM) at 37° C. in the presence of 5% $CO_2$ for 24 hours. The cells were incubated in the culture medium containing 7.5 µM Fura2-AM, 20 mM 2-[4-(2-hydroxyethyl)-1-piperazinyl] ethanesulfonic acid (HEPES) and 2.5 mM probenecid, at 37° C. for about 60 minutes. The Fura2-AM-loaded cells were washed once with assay buffer (Hank's buffer containing 20 mM HEPES), and the $LTD_4$-induced intracellular calcium influx was measured using a FDSS2000 (manufactured by Hamamatsu Photonics K.K.). The crystalline forms of the present invention were treated 30 minutes prior to $LTD_4$ stimulation, and time-course changes of the response provoked by 100 nM of $LTD_4$ was measured over 150 seconds. The receptor antagonistic activity of the crystalline forms of the present invention were evaluated in terms of a maximum fluorescence intensity obtained up to 150 seconds after $LTD_4$ stimulation, and a 50% inhibitory concentration (($IC_{50}$) was calculated for each compound.

As a result, type C crystal of compound I (the compound was prepared in Example 12), type B crystal of compound II (the compound was prepared in Example 14), and type C crystal of compound III (the compound was prepared in Example 16) showed $IC_{50}$ values of 44, 2.8, and 15 nM, respectively.

Biological Example 3

Effects of Compounds on $LTD_4$-Induced Bronchoconstriction in Guinea Pigs

Guinea pigs were anesthetized by injection of pentobarbital sodium (75 mg/kg, i.p.), and a polyethylene cannula was inserted into the trachea which had been incised. For the purpose of administration of $LTD_4$, a catheter was inserted into the jugular vein of the animal. One side of the cannula inserted into the trachea was connected with a volume-controlled respirator to perform artificial respiration at a ventilation volume of 5 mL and at a ventilation rate of 70 times/min. $LTD_4$ was administrated intravenously to induce the bronchoconstriction, and the airway resistance was measured using the Konzett-Rossler method. The bronchoconstriction response was measured for 10 minutes after $LTD_4$-challenge, and the ratio of bronchoconstriction response was determined and represented as a percentage of the maximal increase in insufflation pressure achieved by clamping off the trachea. In this connection, the crystalline forms of the present invention were orally administered 1, 2, 4, 8, 12, 18, 24, 36 and 48 hours prior to challenge by $LTD_4$. In the present Example, the bronchoconstriction inhibition ratio of greater than 95% was evaluated as complete inhibition of bronchoconstriction. Tables 6 and 7 show the results for oral administration of test compounds 2 and 24 hours prior to challenge by $LTD_4$.

As a result, it can be seen that the crystalline forms of the present invention as an ethynylindole compound having a triple bond exhibit complete inhibition of the bronchoconstriction in guinea pigs, in case of oral administration, as shown in Table 6. Furthermore, it was demonstrated that the triple-bond ethynylindole compound exhibits complete inhibition of the bronchoconstriction not only for the administration of the compound 2 hours prior to challenge by $LTD_4$, but also for the administration of the compound 24 hours prior to the challenge by $LTD_4$. In Table 6, the parenthesized numeral represents a dose of the test compound, and the numerals within the table represent inhibition ratios (%).

TABLE 6

|  | Example 12 (1 mg/kg) | Example 14 (1 mg/kg) | Example 16 (1 mg/kg) |
| --- | --- | --- | --- |
| Administered 2 hours prior to LTD4 challenge | 99.5 | 98.5 | 99.6 |
| Administered 24 hours prior to LTD4 challenge | 98.7 | 99.2 | 98.1 |

Namely, it was demonstrated that the crystalline form as an ethynylindole compound having a triple bond is a compound having long-acting effects even upon oral administration, and is useful as an oral therapeutic agent for respiratory diseases.

And now, 4,4'-{4-fluoro-7-[(E)-2-{4-[4-(3-fluoro-2-methylphenyl)butoxy]phenyl}vinyl]-2-methyl-1H-indole-1,3-diyl}dibutanoic acid described in Comparative Example 2 of Patent Document 3 (hereinafter, sometimes abbreviated to Comparative Example 4), 4,4'-{2-methyl-7-[(E)-2-{4-[4-(pentafluorophenyl)butoxy]phenyl}vinyl]-1H-indole-1,3-diyl}dibutanoic acid described in Comparative Example 1 of Patent Document 3 (hereinafter, sometimes abbreviated to Comparative Example 5) and 4,4'-{4-fluoro-2-methyl-7-[(E)-2-{4-[4-(2,3,4,6-tetrafluorophenyl)butoxy] phenyl}vinyl]-1H-indole-1,3-diyl}dibutanoic acid described in Comparative Example 3 of Patent Document 3 (hereinafter, sometimes abbreviated to Comparative Example 6) are ethenyl indole compounds which each the triple bond moiety shown in Table 6 is a double bond. In this connection, when Comparative Examples 4 to 6 are administrated at the same amount as the compounds of Table 6, an inhibition ratio of bronchoconstriction was measured. As shown in Table 7 below, there was complete inhibition in some cases if administration of the compound was made 2 hours prior to challenge by $LTD_4$, but no complete inhibition was achieved if administration of the compound was made 24 hours prior to challenge by $LTD_4$. In Table 7, the parenthesized numeral represents a dose of the test compound, and the numerals within the table represent inhibition ratios (%).

TABLE 7

|  | Comparative Example 4 (1 mg/kg) | Comparative Example 5 (1 mg/kg) | Comparative Example 6 (1 mg/kg) |
|---|---|---|---|
| Administered 2 hours prior to LTD4 challenge | 97.5 | 98.6 | 53.2 |
| Administered 24 hours prior to LTD4 challenge | 43.2 | 74.1 | 16.1 |

Thermodynamical Stability Test

The thermodynamical stability of each crystalline form of compound I, compound II, and compound III was analyzed by differential scanning calorimetry (DSC). As a result, it was apparent that the crystalline forms of the present invention are ones which have improved thermodynamical stability.

For example, specific DSC data of type A crystal (Comparative Example 1), type B crystal (Example 11) and type C crystal (Example 12) of compound I are shown in FIG. 12, FIG. 2, and FIG. 4, respectively. The endothermic peak of type A crystal, type B crystal, and type C crystal of compound I was 146° C., 127° C., and 157° C., respectively, in which the melting point of type C crystal was the highest of all. Also, the fusion enthalpy of type A crystal, type B crystal, and type C crystal of compound I was 96.3 J/g, 57.2 J/g, and 105.6 J/g, respectively, in which the fusion enthalpy of type C crystal was the highest of all. These results confirm that in compound I, type C crystal was the most thermodynamically stable crystalline form. Type B crystal of compound II and type C crystal of compound III were also thermodynamically stable crystalline forms.

Photostability Test

Each crystalline form of compound I, compound II, and compound III were weighed about 5 mg, and were exposed to light from D65 lamp providing an overall illumination of not less than 1.2 million lux hours and an integrated near ultraviolet energy of not less than 200 W·h/m² under 25° C.±2° C.

As a result, it was apparent that the crystalline forms of the present invention are ones which have improved photostability.

For example, when the appearances of type A crystal and type B crystal of compound II were observed by visual check, the degree of change in color to yellow after test as compared to that of before test was bigger in type A crystal. Therefore, in compound II, it is confirmed that type B crystal was more photostable than type A crystal. Type C crystal of compound I and type C crystal of compound III were also photostable crystalline forms.

Formulation Examples

Formulation Examples applied to practical use of the present invention are shown below.

Formulation Example 1

After the following ingredients were mixed by a conventional method, the mixture was tableted to obtain 10,000 tablets containing 10 mg of active ingredients per one tablet.
  Type B crystal of 4,4'-[2-methyl-7-({4-[4-(pentafluorophenyl)butoxy]phenyl}ethynyl)-1H-indole-1,3-diyl]dibutanoic acid (100 g);
  carboxymethylcellulose calcium (disintegrating agent) (20 g);
  magnesium stearate (lubricant) (10 g);
  microcrystalline cellulose (870 g).

Formulation Example 2

After the following ingredients were mixed by a conventional method, the mixture was filtered through a dust-proof filter, and then 5 mL aliquots were charged into ampoules. The ampoules were autoclaved to obtain 10,000 ampoules wherein each of the ampoules contains 20 mg of the active ingredient.
  Type B crystal of 4,4'-[2-methyl-7-({4-[4-(pentafluorophenyl)butoxy]phenyl}ethynyl)-1H-indole-1,3-diyl]dibutanoic acid (200 g);
  mannitol (2 kg);
  distilled water (50 L).

INDUSTRIAL APPLICABILITY

Type C crystal of compound I, type B crystal of compound II and type C crystal of compound III of the present invention are compounds having superior long-lasting effects in combination with a potent cysLT$_1$/cysLT$_2$ receptor antagonistic activity, and are therefore very useful as a long-acting agent for treating respiratory diseases, in case of oral administration.

Furthermore, type C crystal of compound I, type B crystal of compound II, and type C crystal of compound III can be stably supplied in the production because of its thermodynamical stability, and has improved preservation stability due to improved photostability and humidity stability, and are therefore very useful as a bulk drug of a medicine.

The invention claimed is:

1. A crystal of 4,4'-[4-fluoro-7-({4-[4-(3-fluoro-2-methylphenyl)butoxy]phenyl}ethynyl)-2-methyl-1H-indole-1,3-diyl]dibutanoic acid having at least peaks of about 7.29, 10.24, 12.15, 17.95, and 18.44 at 2θ degree in powdered X-ray diffraction spectrum.

2. The crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to claim 1, having peaks of about 6.41, 7.29, 9.22, 10.03, 10.24, 12.15, 12.59, 13.36, 13.88, 14.15, 14.44, 16.60, 17.33, 17.95, 18.44, 18.86, 19.27, 20.23, 21.10, 21.85, 22.26, 23.11, 23.63, and 24.38 at 2θ degree in powdered X-ray diffraction spectrum.

3. The crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to claim 2, characterized by the chart of powdered X-ray diffraction spectrum shown in FIG. 3.

4. The crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to claim 1, characterized by the chart of differential scanning calorimetry shown in FIG. 4.

5. A crystal of 4,4'-[2-methyl-7-({4-[4-(pentafluorophenyl)butoxy]phenyl}ethynyl)-1H-indole-1,3-diyl]dibutanoic acid having at least peaks of about 5.12, 10.16, 10.51, 14.90, and 20.42 at 2θ degree in powdered X-ray diffraction spectrum.

6. The crystal of 4,4'-[2-methyl-7-({4-[4-(pentafluorophenyl)butoxy]phenyl}ethynyl)-1H-indole-1,3-diyl]dibutanoic acid according to claim 5, having peaks of about 5.12, 8.94, 9.22, 10.16, 10.51, 12.07, 13.07, 13.62, 14.37, 14.90, 15.35, 16.05, 16.92, 17.52, 17.86, 18.61, 19.58, 19.92, 20.42, 21.19, 21.71, 22.03, 22.39, 23.74, and 24.24 at 2θ degree in powdered X-ray diffraction spectrum.

7. The crystal of 4,4'-[2-methyl-7-({4-[4-(pentafluorophenyl)butoxy]phenyl}ethynyl)-1H-indole-1,3-diyl]dibutanoic acid according to claim 6, characterized by the chart of powdered X-ray diffraction spectrum shown in FIG. 5.

8. The crystal of 4,4'-[2-methyl-7-({4-[4-(pentafluorophenyl)butoxy]phenyl}ethynyl)-1H-indole-1,3-diyl]dibutanoic acid according to claim 5, characterized by the chart of differential scanning calorimetry shown in FIG. 6.

9. A crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid having at least peaks of about 5.25, 12.16, 15.08, 17.07, and 21.44 at 2θ degree in powdered X-ray diffraction spectrum.

10. The crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to claim 9, having peaks of about 5.25, 8.12, 8.92, 10.45, 11.19, 12.16, 13.12, 13.51, 14.54, 15.08, 15.65, 16.25, 17.07, 17.80, 18.61, 19.59, 20.21, 20.75, 21.44, 22.23, 22.53, 23.29, and 24.41 at 2θ degree in powdered X-ray diffraction spectrum.

11. The crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to claim 10, characterized by the chart of powdered X-ray diffraction spectrum shown in FIG. 9.

12. The crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to claim 9, characterized by the chart of differential scanning calorimetry shown in FIG. 10.

13. A pharmaceutical composition containing the crystal of 4,4'-[4-fluoro-7-({4-[4-(3-fluoro-2-methylphenyl)butoxy]phenyl}ethynyl)-2-methyl-1H-indole-1,3-diyl]dibutanoic acid according to claim 1, 2, 3 or 4 as an active ingredient.

14. A pharmaceutical composition containing the crystal of 4,4'-[2-methyl-7-({4-[4-(pentafluorophenyl)butoxy]phenyl}ethynyl)-1H-indole-1,3-diyl]dibutanoic acid according to claim 5, 6, 7 or 8 as an active ingredient.

15. A pharmaceutical composition containing the crystal of 4,4'-[4-fluoro-2-methyl-7-({4-[4-(2,3,4,6-tetrafluorophenyl)butoxy]phenyl}ethynyl)-1H-indole-1,3-diyl]dibutanoic acid according to claim 9, 10, 11 or 12 as an active ingredient.

* * * * *